US006333473B1

(12) United States Patent
Sawada et al.

(10) Patent No.: US 6,333,473 B1
(45) Date of Patent: Dec. 25, 2001

(54) ROTARY-PUSH TYPE ELECTRONIC COMPONENT AND ELECTRONIC APPLIANCE USING THE SAME

(75) Inventors: Masaki Sawada; Hiroto Inoue; Hiroshi Matsui, all of Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/469,788

(22) Filed: Dec. 22, 1999

(30) Foreign Application Priority Data

Dec. 25, 1998 (JP) ........................................ 10-368887

(51) Int. Cl.[7] ........................................ A01H 25/00
(52) U.S. Cl. ........................................ 200/4; 200/18
(58) Field of Search ................................ 200/4, 14, 18

(56) References Cited

U.S. PATENT DOCUMENTS

| | | | | |
|---|---|---|---|---|
| 4,580,019 | | 4/1986 | Takahashi . | |
| 6,211,474 | * | 4/2001 | Takahashi .............................. | 200/18 |
| 6,218,635 | * | 4/2001 | Shigemoto et al. ............... | 200/14 X |

FOREIGN PATENT DOCUMENTS

| | | | |
|---|---|---|---|
| 4405962 C1 | | 6/1995 | (DE) . |
| 2260598 A | | 4/1993 | (GB) . |
| 6-349379 | | 12/1994 | (JP) . |
| 10-2058589 | | 8/1998 | (JP) . |
| 10-312728 | * | 11/1998 | (JP) . |

* cited by examiner

*Primary Examiner*—Renee Luebke
(74) *Attorney, Agent, or Firm*—Wenderoth, Lind & Ponack, L.L.P.

(57) ABSTRACT

A rotary-push type electronic component is provided for use in an electronic appliance such as a mobile phone. The electronic component includes a base unit, a frame mounted to the base unit, a support shaft coupling the frame to the base unit for pivotal and vertical movement of the frame relative to the base unit, a generally cylindrical operation knob rotatably mounted to the frame, a rotary operation device for emitting an electric signal upon rotation of the generally cylindrical operation knob, and a pair of self-restoring push operation parts spaced apart on the base unit below the frame so as to be operated by pivoting of the frame about the support shaft relative to the base unit. The support shaft is disposed at a rear portion of the frame, and the push operation parts are disposed beneath a front portion of the frame.

22 Claims, 23 Drawing Sheets

ROTARY-PUSH TYPE ELECTRONIC COMPONENT AND ELECTRONIC APPLIANCE USING THE SAME

FIELD OF THE INVENTION

The present invention relates to a rotary-push type electronic component used mainly in an electronic appliance such as a mobile telephone, which allows for rotation of a circumferential portion of a cylindrical operation knob projecting from the operation surface of the appliance in the tangential direction and also for pushing in the direction toward the rotary central axis of the knob, and an electronic appliance using such rotary-push type electronic component.

BACKGROUND OF THE INVENTION

Hitherto, as this kind of rotary-push type electronic component, a rotary encoder with push switch (hereinafter called REPS) 1 as shown in a perspective outline view in FIG. 19 has been known. FIG. 20 is a side sectional view of the REPS 1. Hereinafter, the conventional REPS is explained by referring to FIG. 19 and FIG. 20.

In this REPS 1, a rotary operation part such as a rotary encoder 3 and push operation part such as a push switch 4 are disposed on a mounting substrate 2 which has contacts. The rotary encoder 3 is designed to be movable in a vertical direction V in a specified range.

The push switch 4 is fixed so as not to move.

The rotary encoder 3 comprises:

- a slide contact element 5 held by the mounting substrate 2 so as to be movable in the vertical direction V in the specified range,
- a rotating element 7 rotatably held by a center shaft 6, and
- a cylindrical operation knob 8 fitted to the shaft 6 so as to rotate the rotating element 7.

A plate spring 9 projecting from the lower end of the slide contact element 5 elastically contacts with a pin protrusion 10 at the front side of the mounting substrate 2, such that the rotary encoder 3 is normally urged upwardly to a position remote from the push switch 4.

An operation button 11 of the push switch 4 is provided at a side of the mounting substrate 2 opposite the rotary encoder 3 so as to abut against a pushing part 6A of the shaft 6 of the rotary encoder 3.

The operation of this conventional REPS 1 is described below.

First, an electric signal of the rotary encoder 3 is generated when the rotating element 7 is rotated about the shaft 6, by applying a force in the tangential direction H (FIG. 19) on the outer upper surface 8A of the cylindrical operation knob 8 so as to rotate the cylindrical operation knob 8.

An electric signal of the push switch 4 is generated when the operation button 11 is pushed by the pushing part 6A of the shaft 6, by applying a pushing force in the downward direction V toward the center on the outer upper surface 8A of the cylindrical operation knob 8 sufficient to overcome the urging force of the plate spring 9, so as to move the entire rotary encoder 3.

When the pushing force applied to the cylindrical operation knob 8 is removed, the rotary encoder 3 is pushed back to its normal position by an elastic restoring force of the plate spring 9.

When this REPS 1 is used in a mobile telephone 12, it is often combined, with a two-circuit push switch 13 as shown in a perspective outline view of the mobile telephone in FIG. 21.

The two-circuit push switch 13 is shown in a partially sectional front view of FIG. 22. Two self-restoring push switches 15A, 15B disposed at a specific interval on a switch substrate 14 are designed to operate individually by pushing the top of an operation key 16 rotatably supported by a support member 14A at the center of the switch substrate 14.

The method of use of the mobile telephone 12 shown in FIG. 21 is explained below.

Upon start of use of the mobile telephone 12, a menu of plural function items is displayed in a specified sequence on a liquid crystal display unit 17 of its operation surface 12A.

In this state:

1. A force in the radial direction is applied to the portion (i.e. the outer upper surface 8A) of the cylindrical operation knob 8 of the REPS 1 projecting from the operation surface 12A.
2. By rotating the outer upper surface 8A of the knob 8 in a direction tangentially of the knob, a signal is generated from the rotary encoder 3.
3. Based on the signal, the function item menu on the display screen is displayed. Rotation of the knob 8 causes scrolling through the menu to the line of the desired item.
4. By pushing the left upper surface 16A or the right upper surface 16B of the operation key 16 of the two-circuit push switch 13, the corresponding push switch 15A or 15B is operated.
5. As a result, the function item menu on the display screen is moved through in right or left directions to the column of the desired item, so that the desired item can be selected.
6. For example, at the position of the item "Send", the outer upper surface 8A of the cylindrical operation knob 8 of the REPS 1 is pushed down towards the center axis of the knob. By this operation, the "Send" function is determined.
7. Once the "Send" function is determined, a menu of plural transmission destinations is displayed on the liquid crystal display unit 17 in a specified sequential order.
8. Again, a force in the forward or backward tangential direction (i.e. toward or away from the display unit 17 in FIG. 21) is applied to the outer upper surface 8A of the cylindrical operation knob 8 of the REPS 1 to rotate the knob 8.
9. As a result of the knob rotation, the transmission destination menu is scrolled through in forward or backward directions to the position of the desired destination.
10. At the position of the desired destination, the outer upper surface 8A of the cylindrical operation knob 8 of the REPS 1 is pushed again toward its center axis, to determine the destination of the call.
11. Then a call signal is sent to this selected destination.

Thus, in a downsized electronic appliance such as the mobile telephone 12 comprising such conventional REPS, both the REPS 1 and the two-circuit push switch 13 are used. The user selects a desired item by moving through the menu composed of plural selection items included in the specified sequence in two different directions. In this case, the user must operate both the cylindrical operation knob 8 of the REPS 1 and the operation key 16 of the two-circuit push switch 13 while moving fingers between them. Therefore, the conventional REPS was difficult to control.

In the downsized electronic appliance such as the mobile telephone 12, it was disadvantageous for purposes of layout design of the operation surface to dispose two electronic components for selection of function items on the operation surface 12A.

SUMMARY OF THE INVENTION

The invention is intended to solve the conventional problems in an electronic appliance which is used by selecting a desired item from a menu having plural selection items. It is hence an object of the invention to present a rotary encoder with push switch (REPS), that is, a rotary-push type electronic component excellent in controllability and with which it is possible to select and determine a desired item easily and quickly by moving through a menu composed of plural selection items in different directions by using one operation knob only.

To solve the problems, the REPS of the invention comprises:

a rectangular frame rotatable about a support shaft which has one side supported to be movable vertically in a specified range, a cylindrical operation knob rotatably fitted within the frame, a movable contact coupled to one end of the cylindrical operation knob, and a fixed contact disposed in the frame so as to be engaged with the movable contact, a rotary operation part for emitting an electric signal by rotation of the cylindrical operation knob, and two self-restoring push operation parts disposed below the frame at a specific interval so as to operate upon rotation of the rectangular frame.

The push operation parts can be operated individually by pushing near the outer upper surface of the cylindrical operation knob at one or the other end thereof. The two push operation parts can be operated simultaneously by pushing the outer upper surface of the cylindrical operation knob at a center portion thereof. With regard to operation of these push operation parts (also referred to as switches), the term "simultaneously" is understood to mean either simultaneous or nearly simultaneous such that it can be detected as being simutaneous.

Accordingly, in the electronic appliance used by selecting a desired item from the menu of plural selection items, the invention provides REPS which is excellent in controllability and allows for selecting and determining a desired item easily and quickly by moving through the menu composed of plural selection items in two different directions by using one operation knob only.

DETAILED DESCRIPTION OF THE EXEMPLARY EMBODIMENTS

Figure 1:
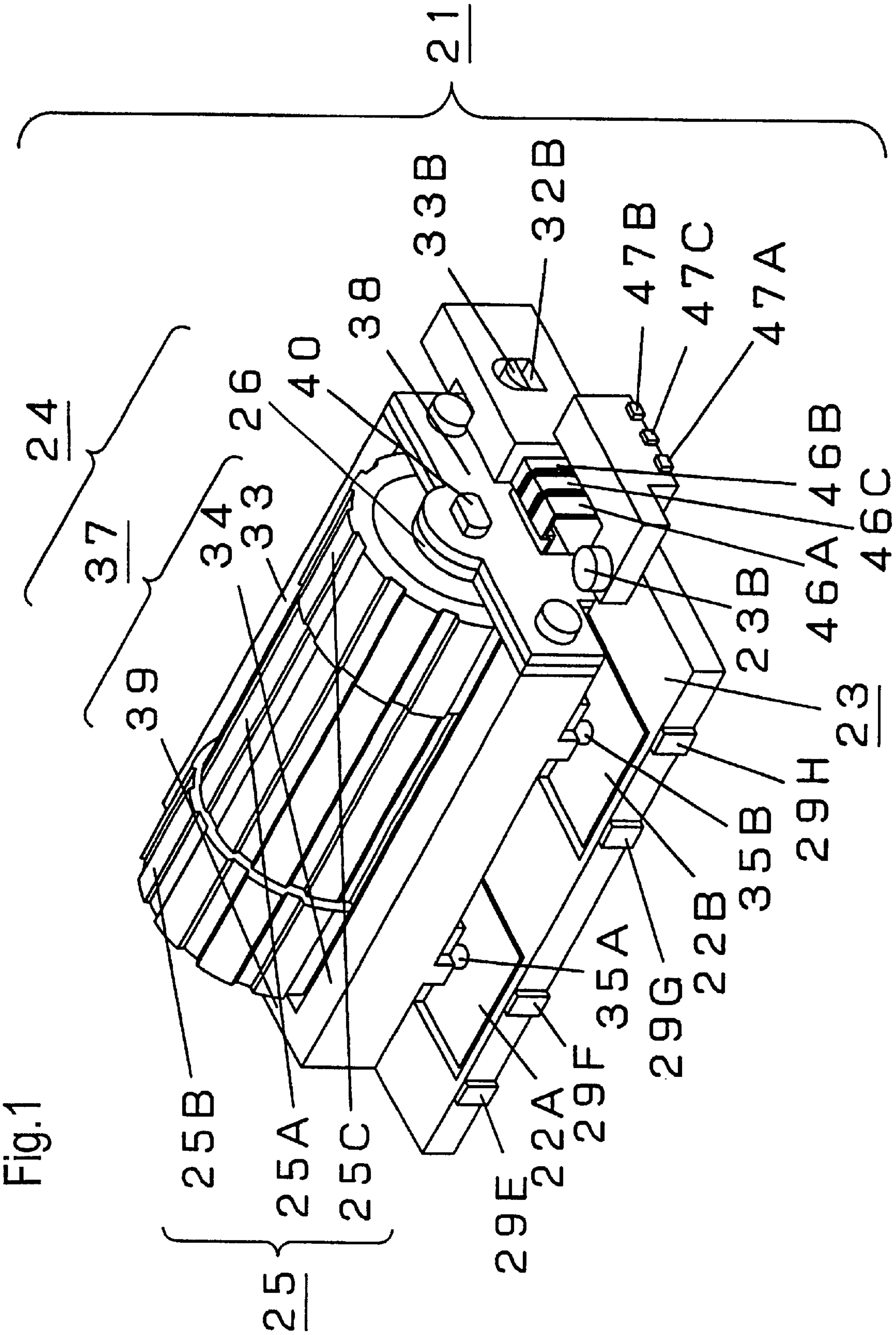
FIG. 1 is a perspective outline view of a rotary encoder with push switch (REPS) according to a first embodiment of the present invention.

Referring now to the drawings, exemplary embodiments of the invention are described in detail below.

First Embodiment

A rotary encoder with push switch (REPS) which is a rotary-push type electronic component according to the first embodiment of the invention is described below mostly with reference to FIGS. 1–4.

As shown in FIG. 1, this rotary encoder with push switch (REPS) 21 comprises:

a. a resin base unit 23 having two push operation parts such as single push switches 22A, 22B, b. a rectangular frame 24 rotatably supported on the base unit 23, and a cylindrical operation knob 25 rotatably supported on this frame 24, c. a rotary operation part such as a rotary encoder 27 (not shown in FIG. 1) is disposed between one end of the knob 25 and a plate element 26 at one end of the frame 24, and d. a contact block 28 coupled to the rotary encoder 27.

Figure 2:
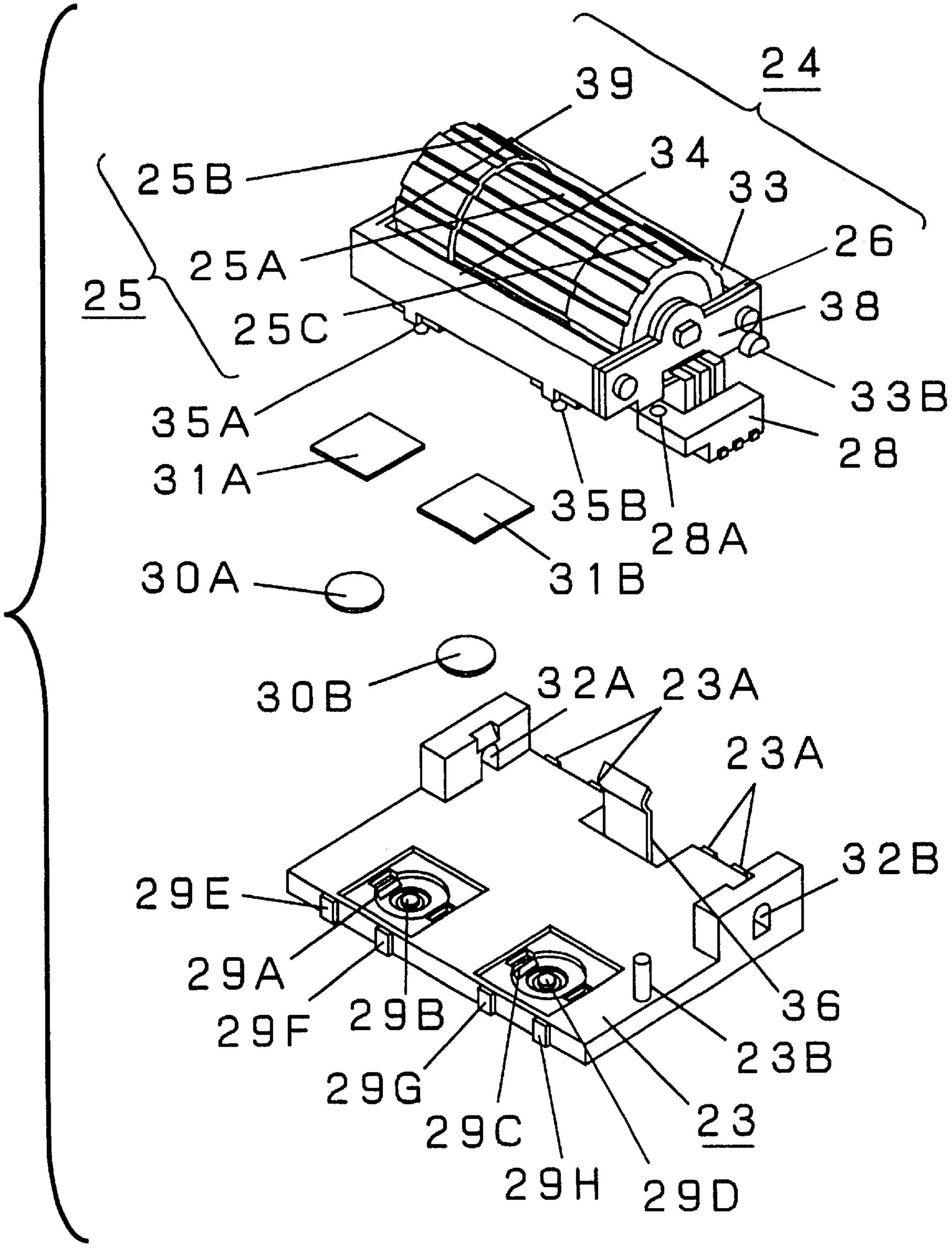
FIG. 2 is a perspective exploded view of the first embodiment.
Figure 3:
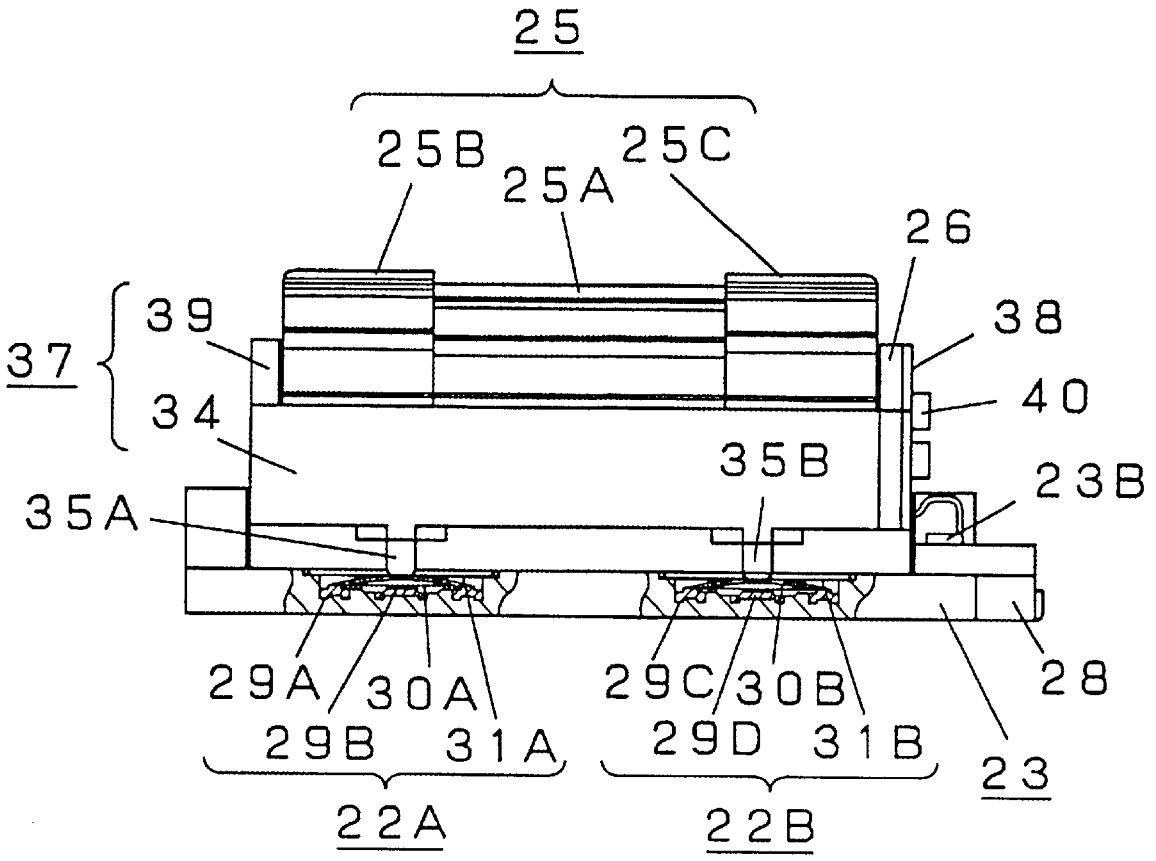
FIG. 3 is a partially sectional front view of the first embodiment.

The two switches 22A, 22B are disposed at a specific interval at the front end of the top of the base unit 23 as shown in FIG. 2 and FIG. 3. For example, the switch 22A is composed of:

fixed contacts 29A, 29B, a dome spring type movable contact 30A made of an elastic thin metal plate, and a flexible film 31A.

The flexible film 31A coated with an adhesive on the lower surface is adhered to the top of the dome spring type movable contact 30A.

The switch 22A has connection terminals 29E, 29F electrically connected with the fixed contacts 29A, 29B disposed at the front end of the base unit 23.

Similarly, the switch 22B is composed of:

fixed contacts 29C, 29D, a dome spring type movable contact 30B made of an elastic thin metal plate, and a flexible film 31B.

The flexible film 31B coated with an adhesive on the lower surface is adhered to the top of the dome spring type movable contact 30B.

The switch 22B has connection terminals 29G, 29H electrically connected with the fixed contacts 29C, 29D disposed at the front end of the base unit 23.

Thus, the dome spring type movable contacts 30A and 30B have nearly the same inverting stroke (i.e. in inverting from convex upwardly to concave upwardly) and inverting operation force.

Figure 4:
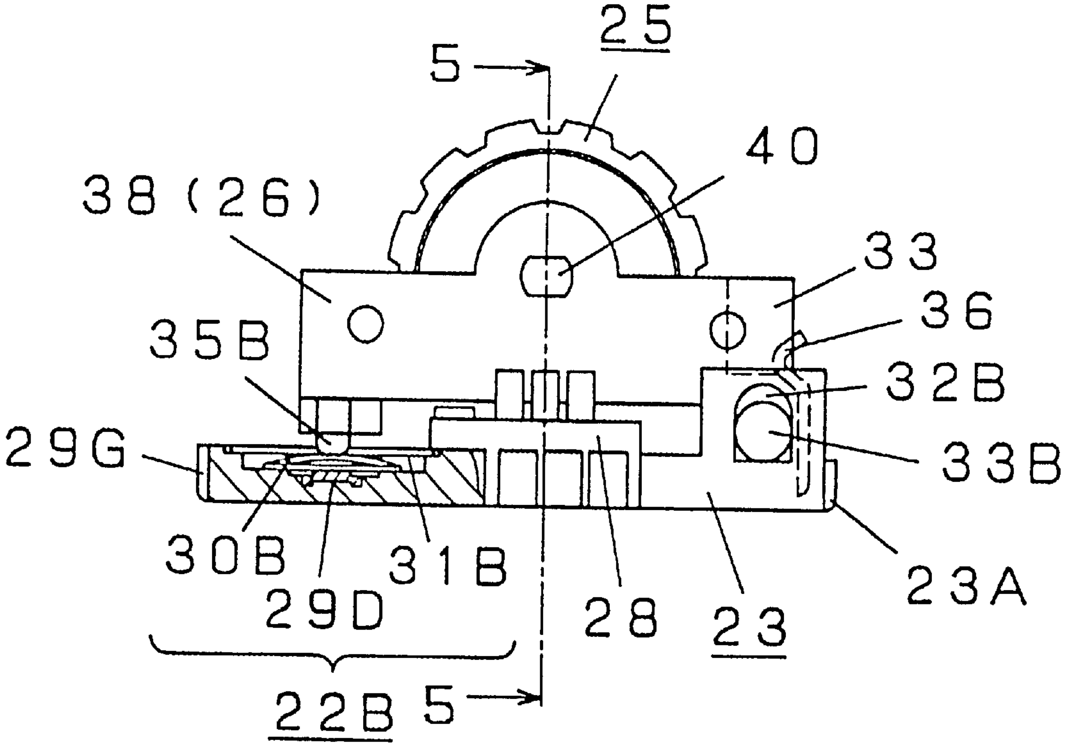
FIG. 4 is a partially sectional side view of the first embodiment.

Moreover, as shown in FIG. 1 and FIG. 2, a pair of support slots 32A, 32B are provided in the base unit 23. Support shafts 33A, 33B are provided at lower parts of both ends near a rear side 33 of the frame 24 and are snapped into the slots 32A, 32B to couple the frame 24 to the base unite 23. With this arrangement, the frame 24 is rotatable about the shafts 33A, 33B and movable vertically in a specified range. As shown in FIG. 3 and FIG. 4, two pushing protrusions 35A, 35B corresponding to the two switches 22A, 22B are provided on the bottom of the frame 24 near its front side 34. In their normal state, the pushing protrusions 35A, 35B abut against the central peaks of the dome spring type movable contacts 30A, 30B of the two switches 22A, 22B through flexible films 31A, 31B, respectively.

As shown in FIG. 4, a spring 36 fixed between the two slots 32A and 32B of the base unit 23 urges the frame 24 downward so that the support shafts 33A, 33B are normally positioned at the lower end of their vertical movable range. The urging force of the spring 36 is set smaller than the urging force of the switches 22A or 22B.

Four terminals 23A (two pieces an each side of the spring 36) are provided at the rear end of the base unit 23 for soldering and fixing the REPS 21 of the invention to a wiring board 51 of an applicable electronic appliance described below.

Referring especially to FIG. 4, FIG. 5, and FIGS. 6A and 6B, the frame 24 and knob 25 are described below.

As shown in FIG. 4, FIG. 5, and FIGS. 6A and 6B, the frame 24 is composed of:

a U-shaped element 37 having a rear side portion 33, a front side portion 34 and a central portion 39 coupling the rear and front side portions 33, 34 together, and having the support shaft 33A provided at the lower, front part of the central portion 39, a plate element 26, having the support shaft 33B, for closing the open end of the U-shaped element 37, and a clamp plate 38 for combining and fixing the U-shaped element 37 and plate element 26 with one another.

The knob 25 is rotatably fitted to a metal shaft 40 held still between a hole in the central portion 39 of the U-shaped element 37 and a hole in the plate element 26. The cylindrical outer circumference of the knob 25 is supported parallel to the sides 33, 34.

The outer diameter of the knob 25 is smaller at its middle portion 25A so that the middle portion 25A is indented relative to the two side portions 25B, 25C. Due to this shape of the knob 25, the user manipulating this rotary-push type electronic component can easily locate and push down the middle portion 25A to operate the two switches 22A, 22B simultaneously.

The interval between the slots 32A, 32B of the base unit 23 is set equal to or, preferably wider than the axial length of the middle portion 25A of the knob 25. In this manner, the indented middle portion 25A,of the knob 25 can be reliably pushed to operate the two switches 22A, 22B.

Referring to FIG. 5, FIGS. 6A and 6B, and FIGS. 7A and 7B, the constitution of the rotary encoder 27 is described below.

The rotary encoder 27 is mainly composed of:

a radially-shaped contact plate 42 movably disposed on the outer side of a rotating element 41, a common elastic contact 43A, and elastic contacts 43B, 43C fitted to the plate element 26, and flexible coupling plates 46A, 46B, 46C made of thin metal plates.

The rotating element 41 is fitted so as to close the opening at the hollow end of the knob 25. The knob 25, rotating element 41, and radially-shaped contact plate 42 rotate integrally. The two elastic contacts 43B, 43C differing slightly in length from the common elastic contact 43A are extended from the plate element 26 facing the radially-shaped contact plate 42. The common elastic contact 43A and elastic contacts 43B, 43C are fixed contacts, and elastically contact with the radially-shaped contact plate 42. By rotating the knob 25, the three elastic contacts elastically slide on the radially-shaped contact plate 42. By this rotation, two electric signals (pulse signals) conforming to the rotating direction are generated between the common elastic contact 43A and two elastic signal contacts 43B, 43C.

At the inner side of the rotating element 41, a radially undulated portion 44 corresponding to the radially-shaped contact plate 42 at the outer side is disposed. A detent 45A of a "click-feeling" spring 45 fixed to the shaft 40 is elastically fitted on this undulated portion 44.

This constitution produces a "click" feeling corresponding to the generation of an electric signal upon rotation of the knob 25. While the knob 25, that is, the rotating element 41 is not rotating, the detent 45A of the click-feeling spring 45 is fitted in the recess of the radial undulated portion 44, thereby preventing erroneous generation of signals by inadvertent rotation of the knob The electric signals generated between the movable radially-shaped contact plate 42 and the elastic contacts 43A, 43B, 43C are fed to connection terminals 47A, 47B, and 47C at the outer end of the contact block 28 through the flexible coupling plates 46A, 46B, and 46C made of thin metal plates integrally with the elastic contacts.

Figure 7A:
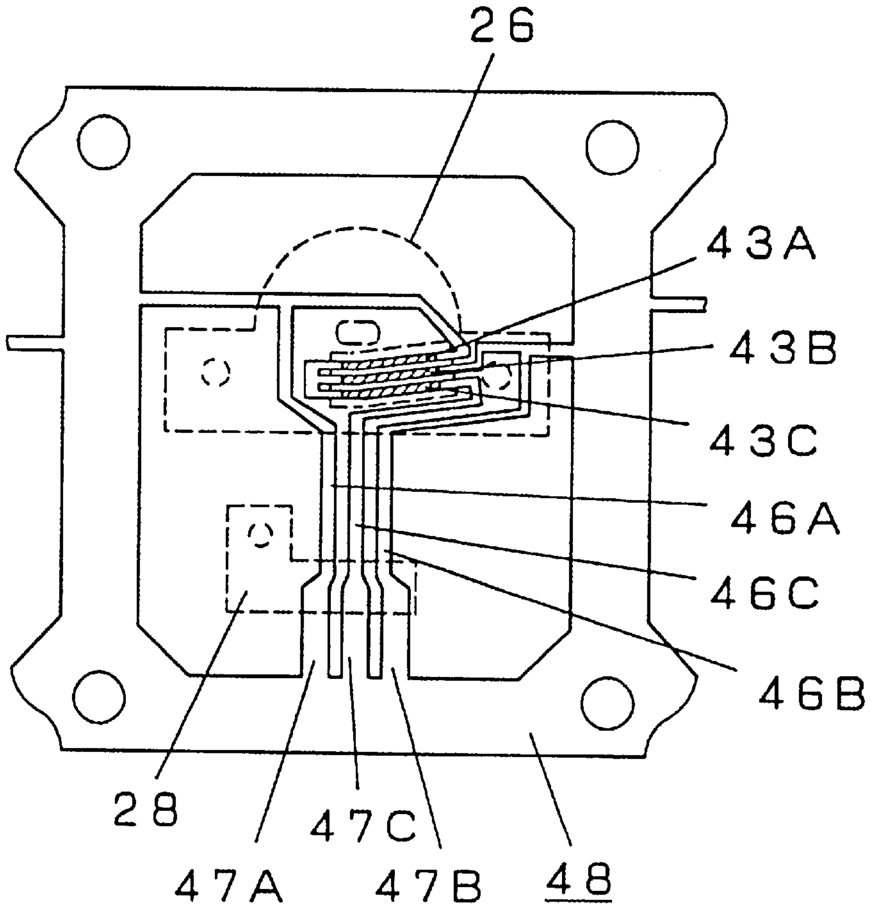
FIG. 7A is an explanatory diagram of a method of forming a plate element and contact block of the first embodiment.
Figure 7B:
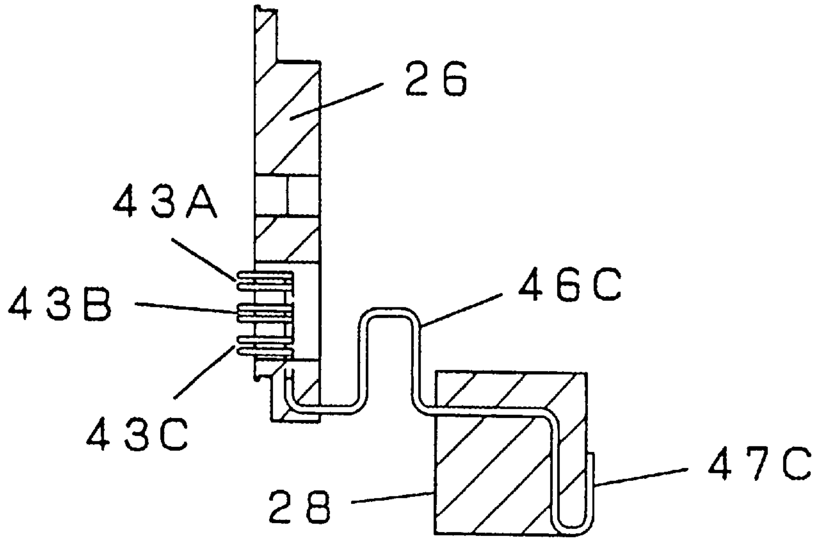
FIG. 7B is a sectional view after cutting and blanking of a thin metal plate portion.

The method of forming the plate element 26 and contact block 28 is explained below. FIG. 7A and FIG. 7B are explanatory diagrams of the method of forming the plate element and contact block. First, FIG. 7A shows a plan view of a thin metal plate 48 after a blanking process.

The thin metal plate 48 comprises:

three elastic contacts 43A, 43B, 43C, coupling plates 46A, 46B, 46C, and three connection terminals 47A, 47B, 47C formed at the leading ends of the coupling plates.

When the portions of the block 28 and plate element 26 are molded by resin as indicated by dotted lines in FIG. 7A, the thin metal plate 48 is insertmolded in block 28 and plate element 26. FIG. 7B shows a sectional view after cutting and blanking process of the thin metal plate. As indicated by FIG. 7B, the thin metal plate 48 is cut and bent at the portions forming the elastic contacts, so as to form the common elastic contact 43A and two signal contacts 43B, 43C. The three connection terminals 47A, 47B, 47C are cut and bent into specified shapes, and a crank shape is formed in the middle of the coupling plates 46A, 46B, 46C. By thus processing the thin metal plate 48, the thin metal plate 48, plate element 26, and contact block 28 are formed into the shapes conforming to the completed state of the encoder 27.

Figure 5:
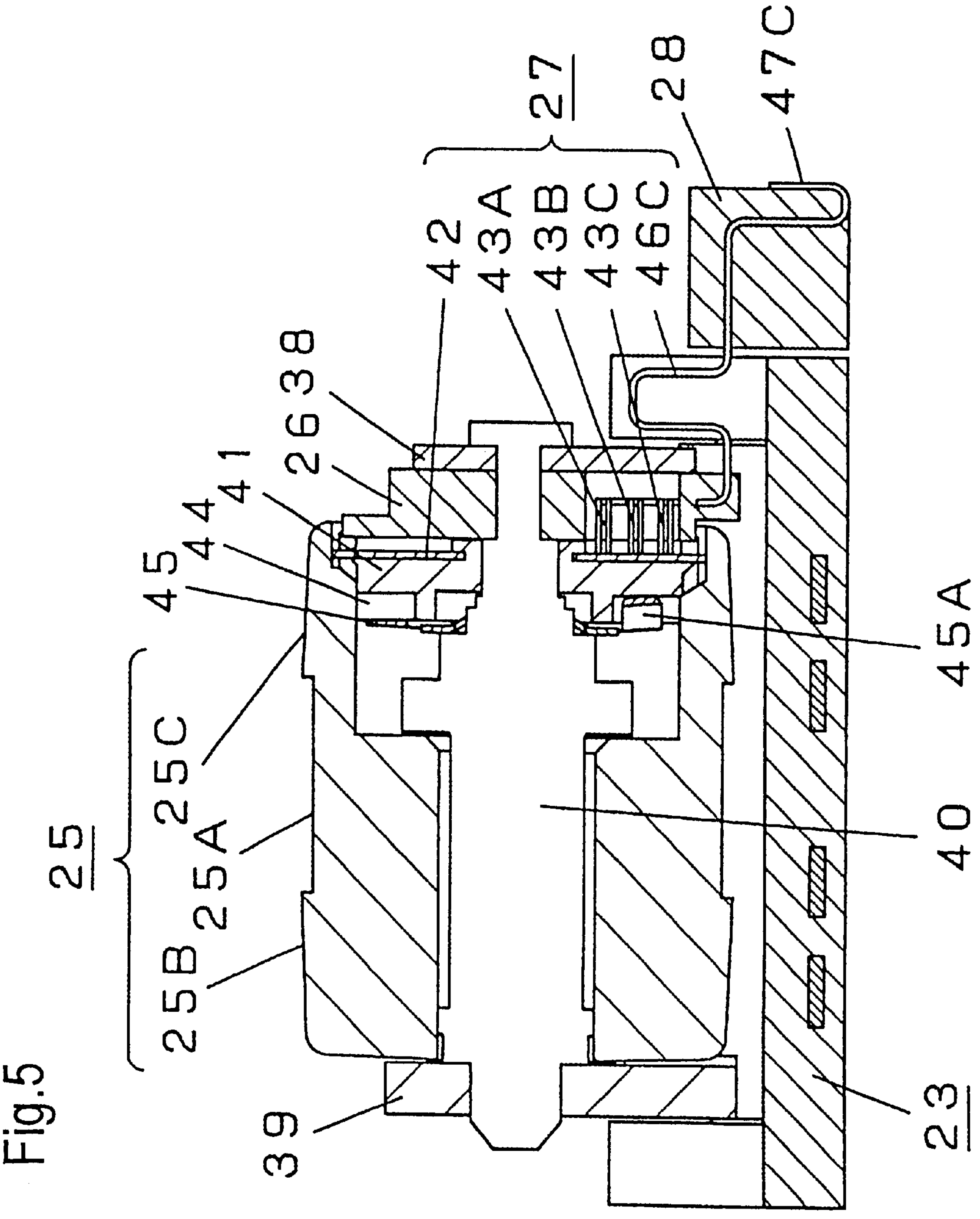
FIG. 5 is a sectional view along line 5—5 of FIG. 4.
Figure 6A:
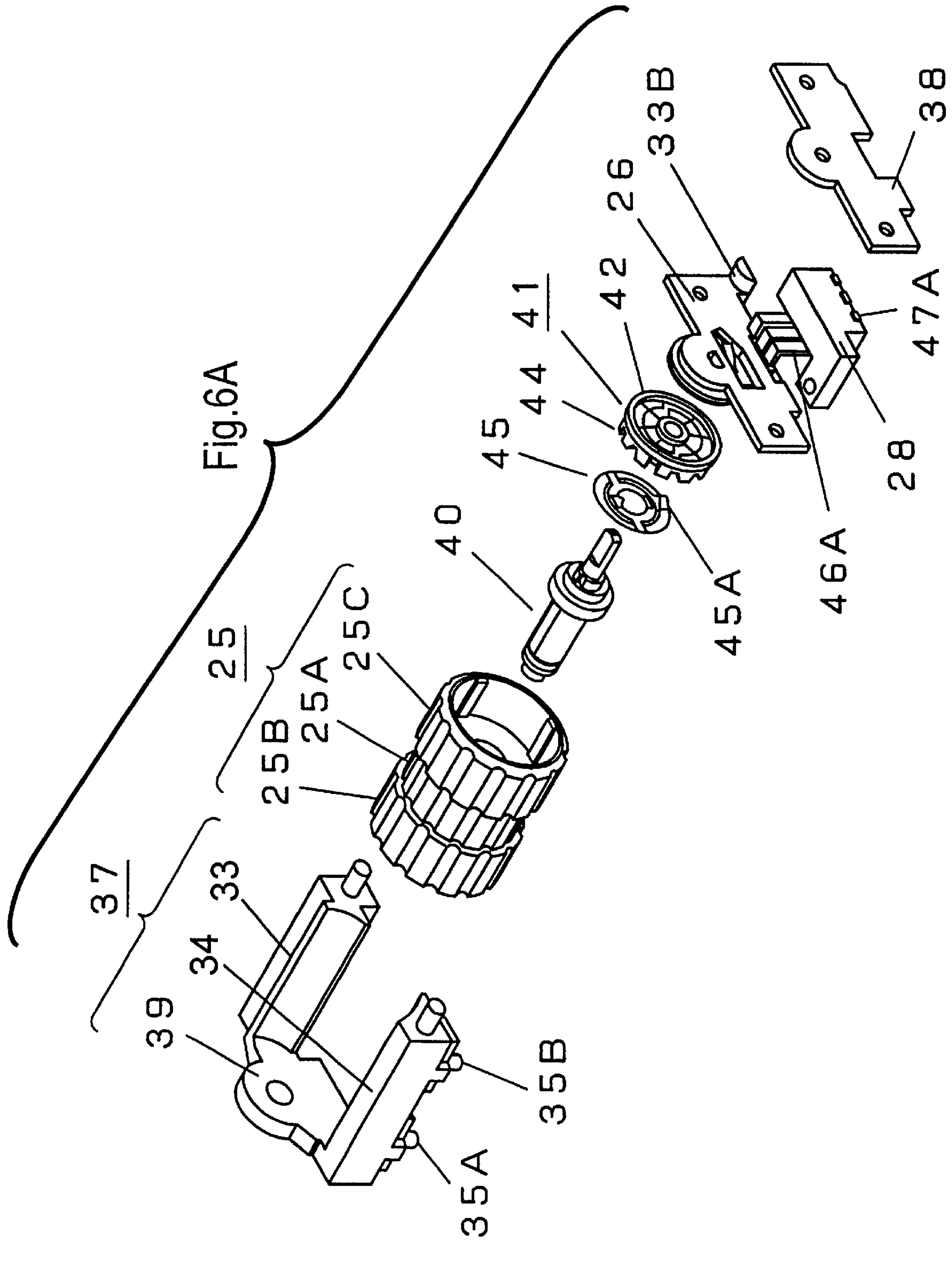
FIG. 6A is a perspective exploded view of a rotary encoder of the first embodiment.
Figure 6B:
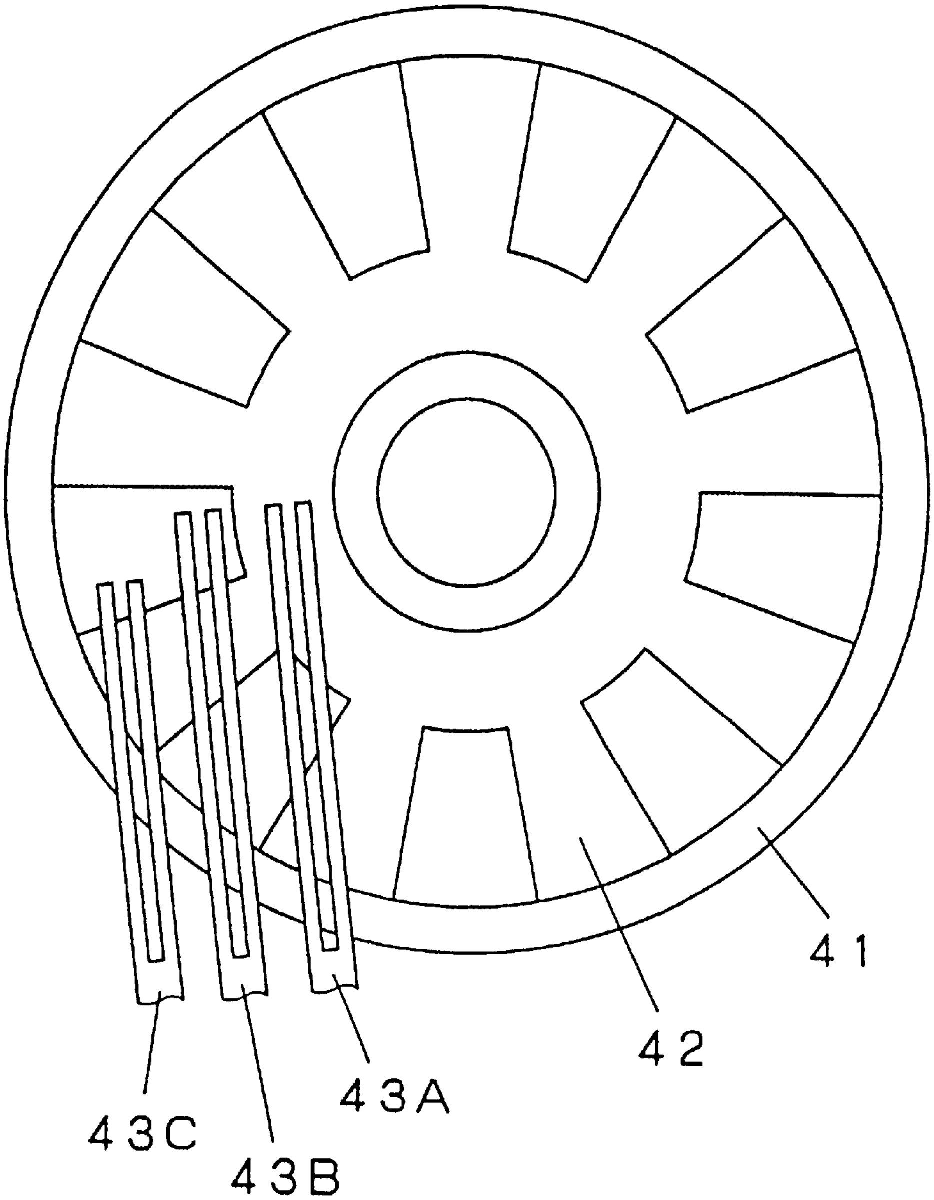
FIG. 6B is a front view of a example that the common elastic contact 43A and elastic contacts 43B, 43C elastically contact with the radially-shaped contact plate 42.

When fitting and supporting the frame 24 in the support slots 32A, 32B of the base unit 23 as shown in FIG. 2, a fixing detent 23B provided at the upper side of the base unit 23 is tightly inserted into a fixing hole 28A in the contact block 28. As a result, as shown in FIG. 3 to FIG. 5, the lower side of the contact block 28 is fixed flush with the lower side of the base unit 23.

Figure 8:
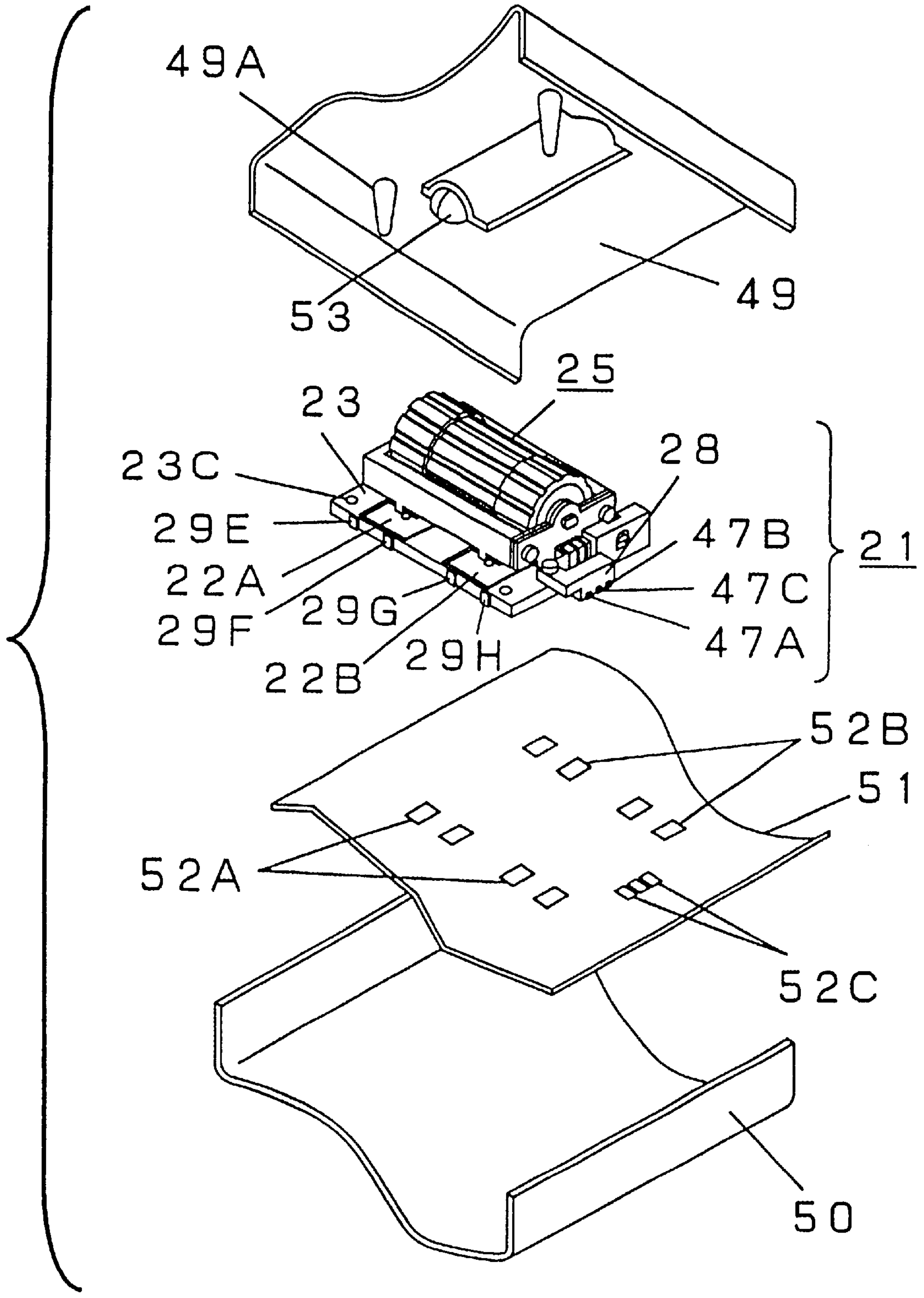
FIG. 8 is a perspective outline view for explaining a method of mounting the REPS on an intended electronic appliance.
Figure 9:
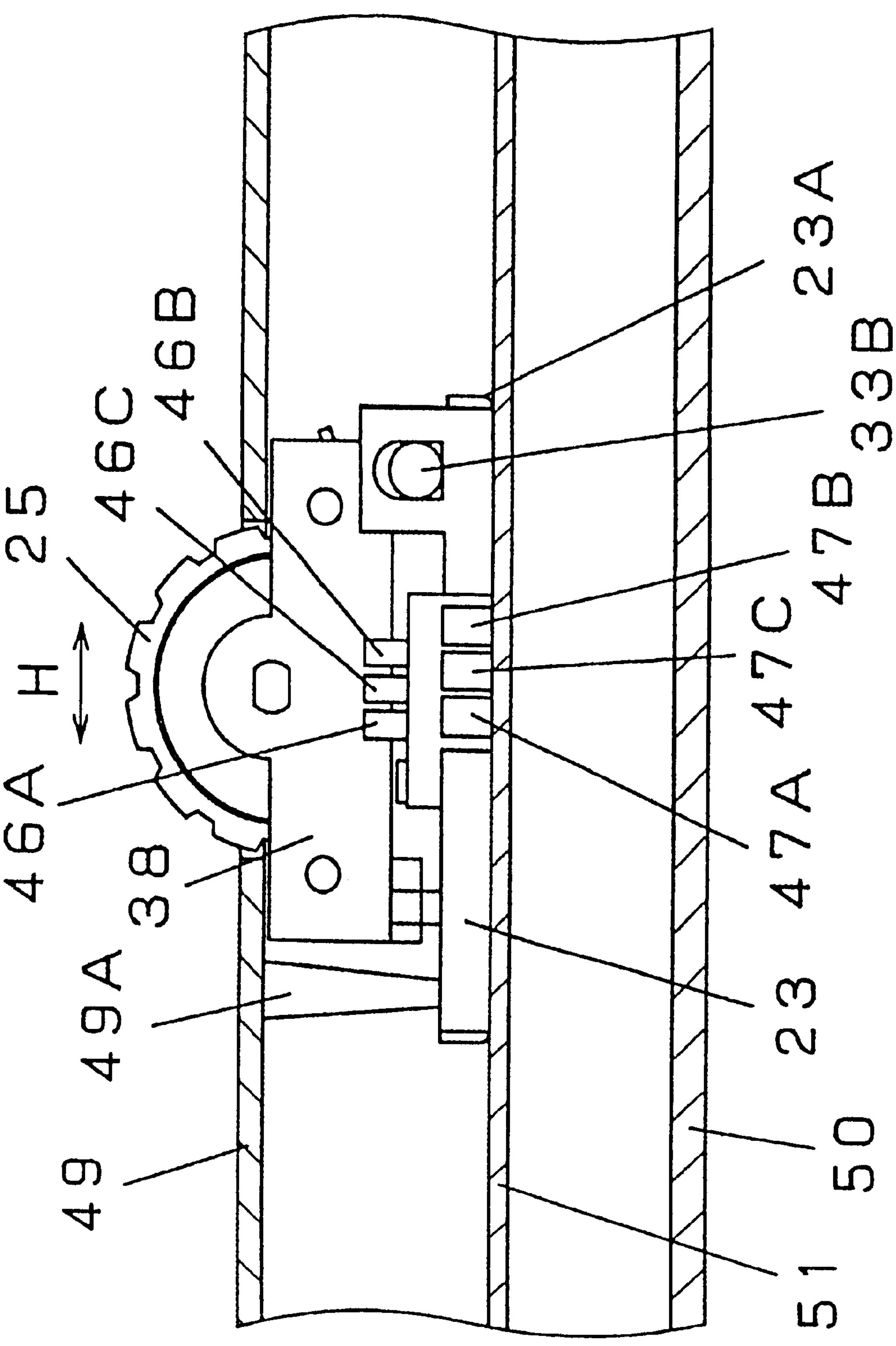
FIG. 9 is a partially sectional side view of the electronic appliance including the REPS of the first embodiment.
Figure 10:
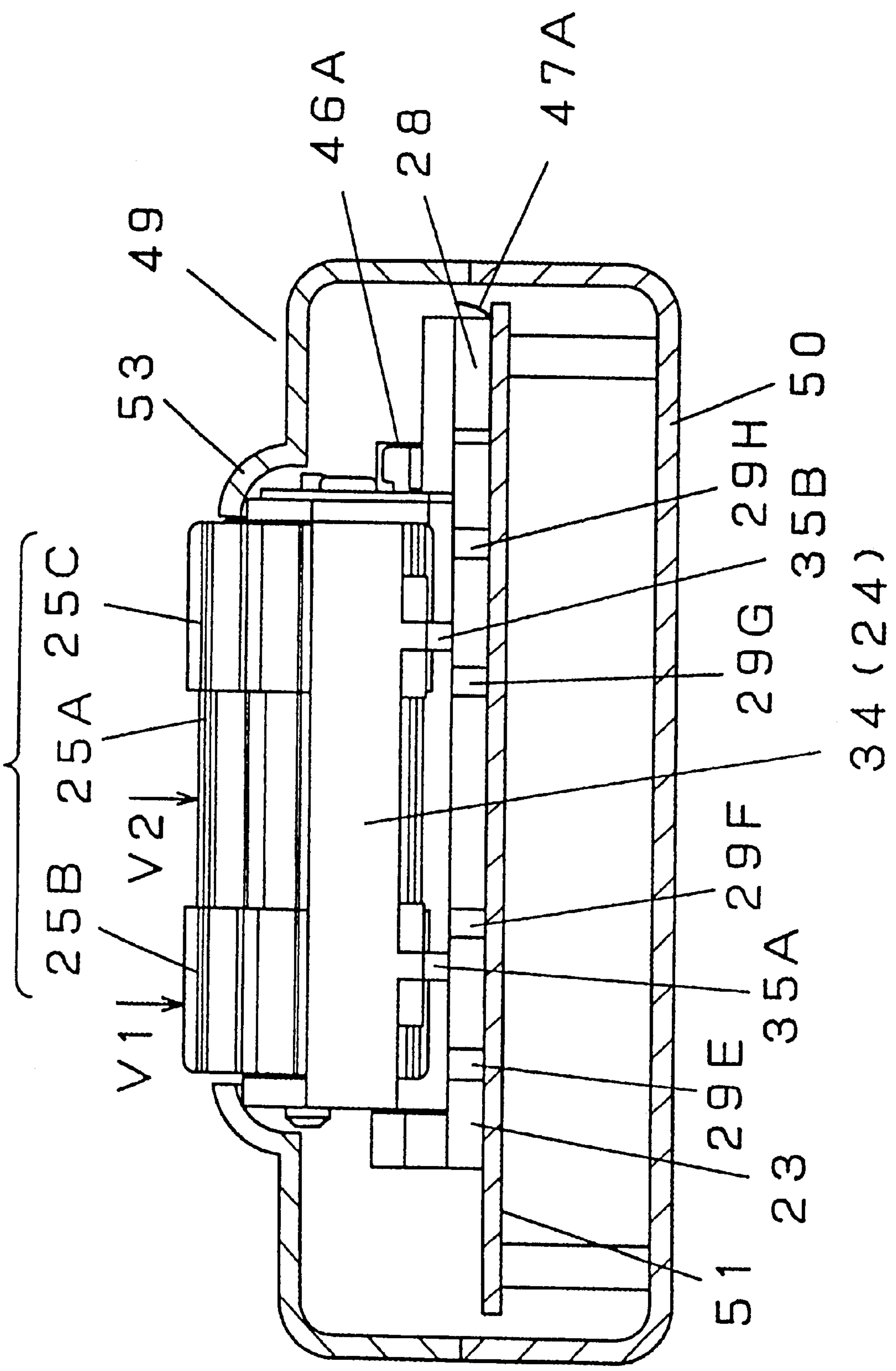
FIG. 10 is a partially sectional front view of the electronic appliance including the REPS of the first embodiment.

FIG. 8 is a perspective outline view for explaining a method of mounting the REPS of the first embodiment on the desired electronic appliance. FIG. 9 is a partially sectional side view of the electronic appliance incorporating the REPS. FIG. 10 is a partially sectional front view of the electronic appliance incorporating the REPS. In FIG. 10, reference numeral 49 represents an upper case of the electronic appliance, reference numeral 50 represents a lower case, and reference numeral 51 represents a wiring board for mounting the electronic components.

As shown in FIG. 8, the REPS 21 of the embodiment is fitted and connected to the wiring board 51 by soldering:

four terminals 29E, 29F, 29G, 29H for the switches 22A, 22B provided at the front end of the base unit 23 to four soldering lands 52A on the wiring board 51 of the electronic appliance, four terminals 23A provided at the rear end of the base unit 23 to four soldering lands 52B on the wiring board 51 of the electronic appliance, and three connection terminals 47A, 47B, 47C at the lower side of the contact block 28 to soldering lands 52C on the wiring board 51 of the electronic appliance, respectively.

The wiring board 51 mounting the REPS 21 is installed in the electronic appliance by inserting and fixing it between the upper case 49 and lower case 50.

At the lower side of the upper case 49 of the electronic appliance, two protruding elongated conical bosses (positioning engaging parts) 49A are formed. Two round holes 23C are formed in the base unit 23 of the REPS 21 of the embodiment When inserting and fixing the wiring board 51 between the upper case 49 and lower case 50 of the electronic appliance, the bosses 49A are inserted into the round holes 23C. As a result, the upper case 49 of the electronic appliance and the REPS 21 can be accurately positioned when assembled. By this accurate positioning, the electronic appliance can be manipulated stably and accurately, and the appearance of the electronic appliance is improved.

Or, as shown in FIG. 9 and FIG. 10, in the state of the REPS 21 of the embodiment installed in the electronic appliance, the upper half of the cylindrical shape of the knob 25 is projecting from the upper case 49 of the electronic appliance. Both ends of the knob 25 are covered with hemispherical covers 53 formed integrally with the upper case 49 of the electronic appliance.

In this arrangement, the controllability of the knob 25 is improved, the height dimension of the upper case 49 of the electronic appliance is reduced, invasion of dust into the electronic appliance from the end of the knob 25 can be prevented, and the appearance of the top of the upper case 49 which is the operating surface of the electronic appliance is enhanced.

The operation of the REPS of the embodiment is described below.

First, with reference to the partial sectional views of FIGS. 9 and 10 showing of the electronic appliance having the REPS of the embodiment, the operation is as follows.

1. The user applies a force to the upper end portion of the indented middle portion 25A of the outer circumference of the knob 25 projecting from the operating surface of the upper case 49 of the electronic appliance, in the tangential direction (the direction of arrow H in FIG. 9), to rotate the knob 25;
2. By this rotation, the rotating element 41 coupled to the end of the knob 25 is rotated (see sectional view in FIG. 5);
3. The common elastic contact 43A and two elastic signal contacts 43B, 43C extending from the plate element 26 of the frame 24 elastically slide on the radially-shaped contact plate 42 disposed at the outer side of the rotating element 41; and
4. By this elastic sliding, an electric signal (pulse signal) is generated for the rotary encoder 27 according to the rotating direction of the knob 25.

Moreover, at the time of the operation described above,

1. The detent 45A of the click-feeling spring 45 fixed to the shaft 40 elastically slides on the radial undulated portion 44 at the inner side of the rotating element 41;
2. A click feeling conforming to the generation of an electric signal is generated; and
3. When rotation of the knob 25 is stopped, the detent 45A is fitted into the recess of the radial undulated portion 44.

The electric signal generated in this operation is sent to the soldering lands 52C of the wiring board 51 of the electronic appliance from the elastic contacts 43A, 43B, 43C through the coupling plates 46A, 46B, 46C and connection terminals 47A, 47B, 47C of the contact block 28, and is transmitted to the circuit of the electronic appliance.

Incidentally, the position for applying a force to the knob 25 in the tangential direction in this operation is not limited to the upper end of the middle 25A of the knob 25. The position may be deviated to the right or left side of the knob 25. However, due care is needed not to press the knob 25 by mistake when applying a force in the tangential direction. Manipulation of the middle 25A minimizes the chance of pushing the knob 25 by mistake.

Figure 11:
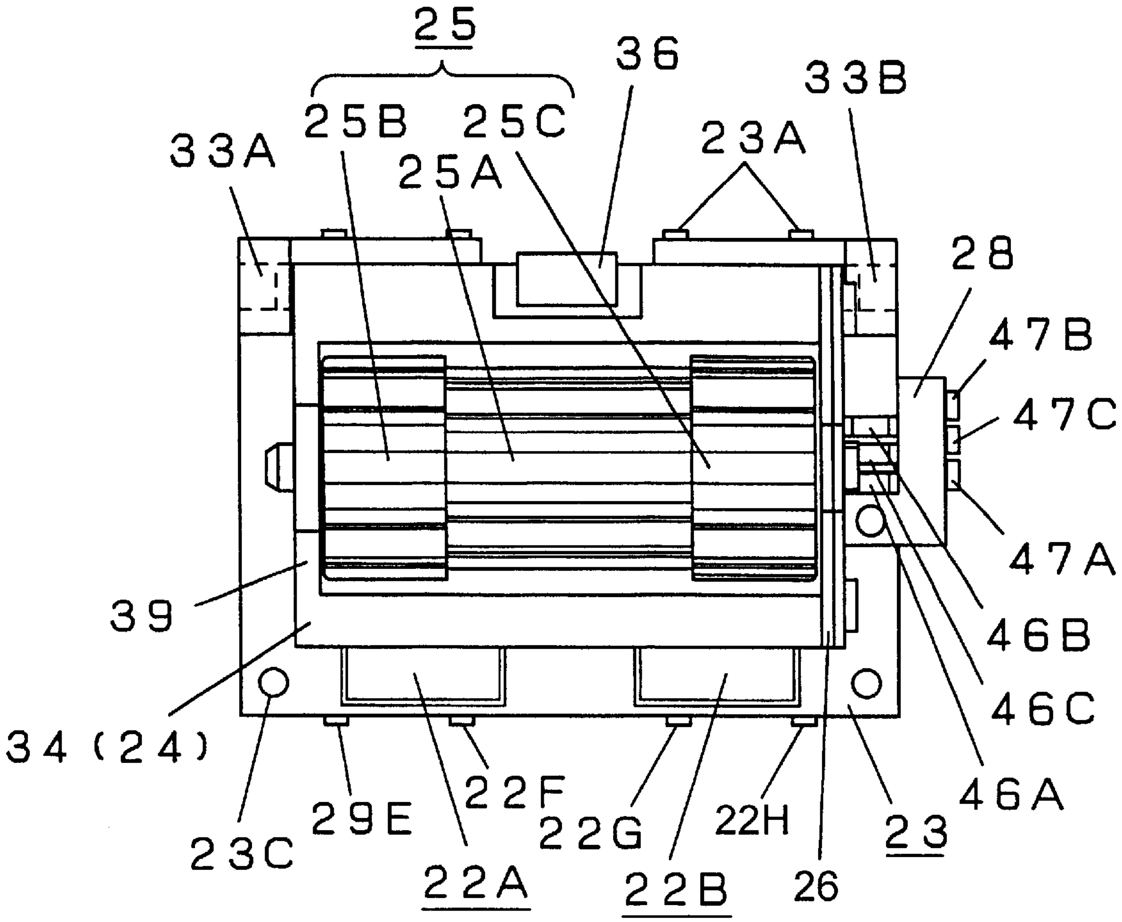
FIG. 11 is a top view of the REPS of the first embodiment.

The switch operation is described below while referring to FIG. 9, FIG. 10, and FIG. 11 showing the top of the REPS of the embodiment.

Figure 12:
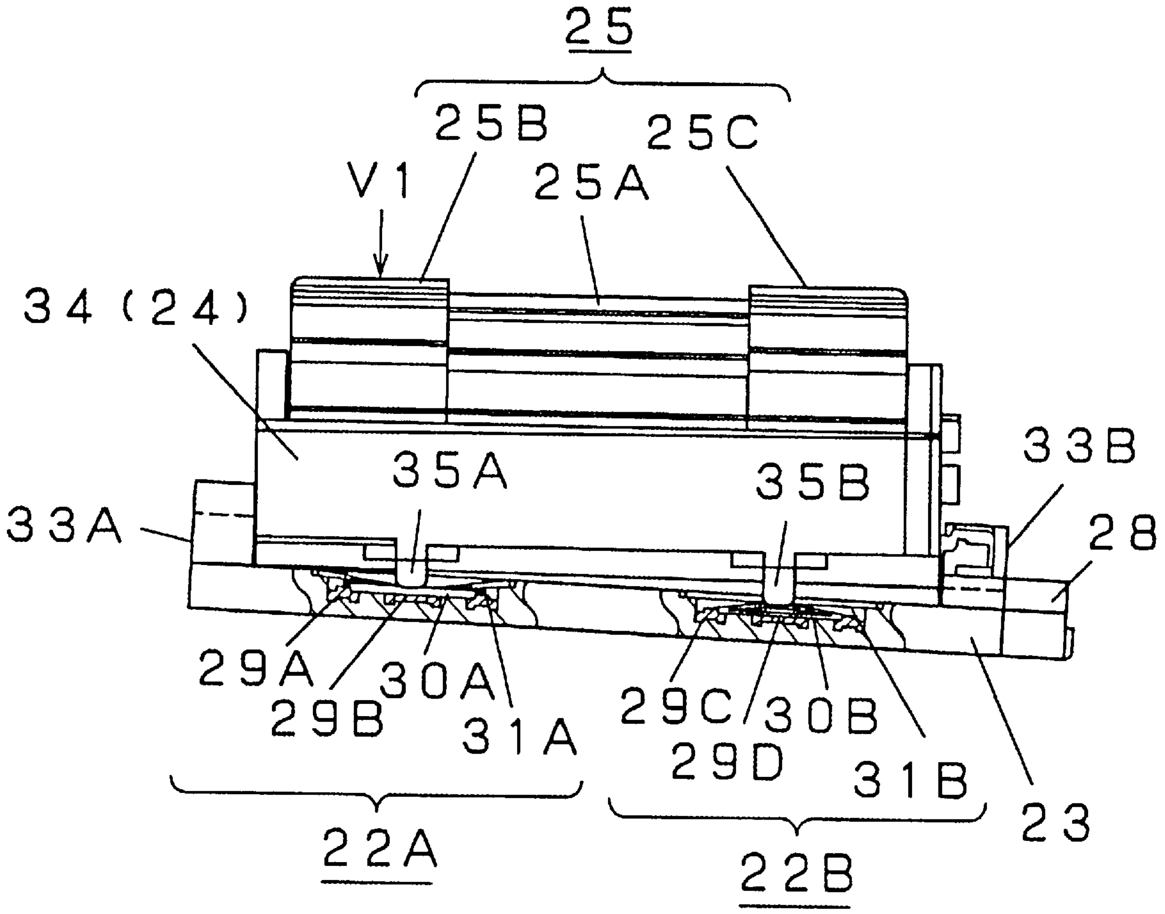
FIG. 12 is a partially sectional front view for explaining the operating state in the case of pushing one side upper surface of the outer circumference of a cylindrical operation knob of the first embodiment.

A pushing force is applied to the upper end portion of one side 25B on the outer circumference of the knob 25 in the direction of arrow V1 (see FIG. 10 and FIG. 12 which are front views showing the operating state of the REPS of the embodiment). By this pushing force, the frame 24 holding the knob 25 swings by rotation of the support shafts 33A, 33B. The pushing force in the direction of arrow V1 acts mostly on the switch 22A which, of the two switches 22A and 22B, the closest to the one side 25B being pushed. Accordingly, the dome spring type movable contact 30A of this switch 22A is pushed down and deflected downward. The frame 24 inclines about a line between one support shaft 33A and the other switch 22B, and when the pushing force becomes larger, the dome spring type movable contact 30A is inverted to short-circuit between the fixed contacts 29A and 29B, thereby turning on the switch 22A.

At this time, the frame 24 overcomes the urging force of the spring 36, and its one support shaft 33B moves upward in its support slot 32B, and this motion is nearly equal to the action stroke of the switch 22A.

When the pushing force applied to the upper end of the side 25B is released, the dome spring type movable contact 30A of the switch 22A returns to the original dome shape by its own elastic restoring force. The switch 22A is placed in an OFF state, and the frame 24 and the knob 25 held by the frame also return to their normal positions shown in FIG. 9.

In this way, by pushing the upper end portion of the side 25B, the switch 22A can be operated.

Similarly, by pushing the upper end portion of the other side 25C of the knob 25, the switch 22B can be operated.

Figure 13:
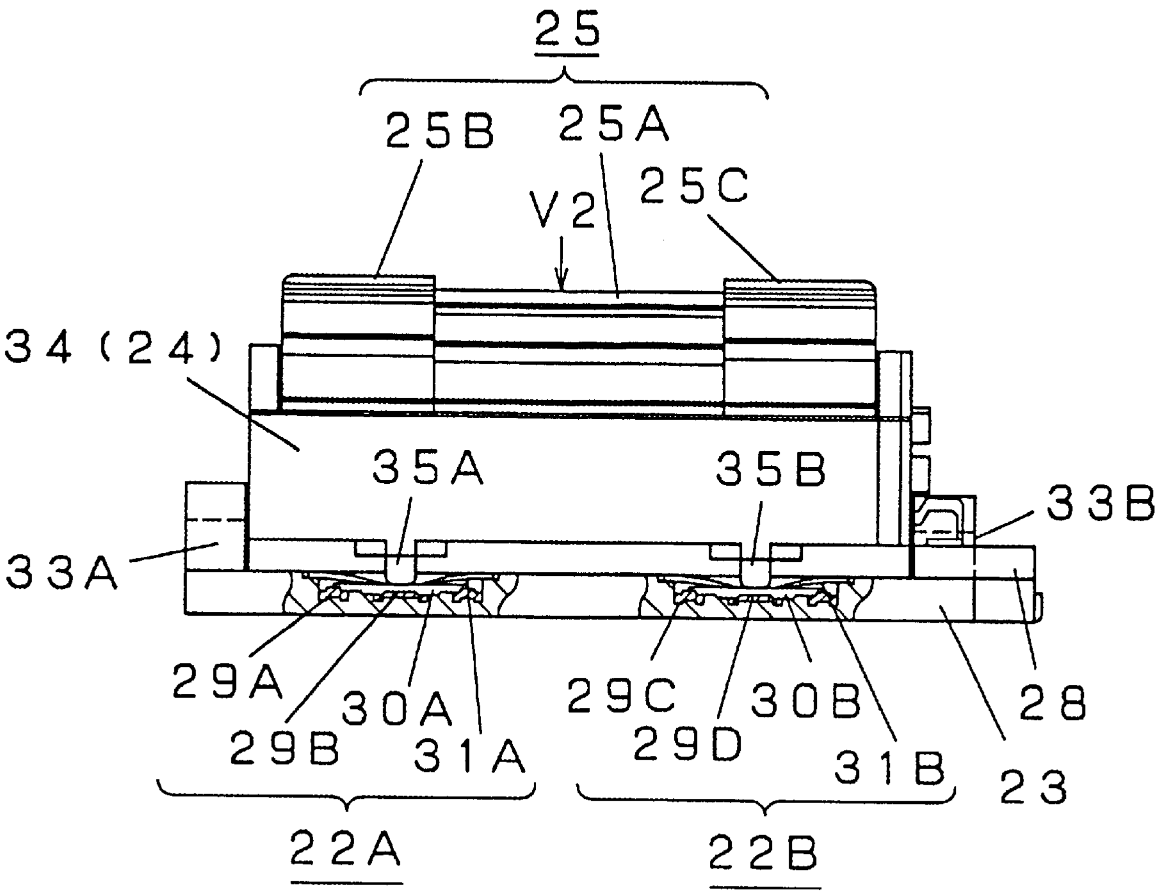
FIG. 13 is a partially sectional front view for explaining the operating state in the case of pushing the middle upper surface of the outer circumference of the cylindrical operation knob of the first embodiment.

Next is explained the operation of applying a pushing force to the upper end portion of the indented middle portion 25A of the outer circumference of the knob 25 in the direction of arrow V2 (see FIG. 9 and FIG. 13 which is a front view showing the operating state of the REPS of the embodiment). By the pushing force in the direction of arrow V2, the frame 24 holding the knob 25 swings by rotation of the support shafts 33A, 33B. The pushing force in the direction of arrow V2 causes the pushing protrusions 35A, 35B at the lower side of the frontside 34 of the frame 24 to push and operate the two switches 22A, 22B on the base unit 23. The pushing force in the direction of arrow V2 acts nearly equally on the two switches 22A, 22B, and the dome spring type movable contacts 30A and 30B of the two switches 22A and 22B are deflected nearly at the same time. Simultaneously, the frame 24 rotates about the central line linking the two support shafts 33A, 33B. As the pushing force increases, the two dome spring type movable contacts 30A, 30B are inverted nearly at the same time. By this inverting action,.as shown in FIG. 13, the fixed contacts 29A and 29B, and 29C and 29D are short-circuited respectively, thereby turning on the switches 22A and 22B.

In this operation, when the two switches 22A and 22B are turned on, the ON timing might be slightly deviated. Accordingly, switching recognition means using time measuring means is provided in order to judge that both switches are ON when the two switches are turned ON within a specified time period. That is, it is intended to distinguish the action of turning on both switches 22A, 22B by pushing the middle portion 25A from the actions of turning on the switch 22A by pushing the side 25B of the operation knob 25 and turning on the switch 22B by pushing the side 25C of the operation knob 25.

In this constitution, when two push operation parts are manipulated within a specific time, the electric signal may be processed differently from the single electric signal when either push operation part is manipulated.

At this time, the support shafts 33A, 33B of the frame 24 are rotated and pushed to the lower ends of the support slots 32A, 32B by the urging force of the spring 36.

When the pushing force applied to the upper end portion of the middle portion 25A of the knob 25 is released, the dome spring type movable contacts 30A and 30B of the switches 22A and 22B return to their original dome shapes due to their own elastic restoring force. The switches 22A and 22B are both turned off, and the frame 24 and the knob 25 held by the frame are also returned to their normal states shown in FIG. 9.

Therefore, as explained above, by pushing the knob 25, the electronic appliance can be manipulated in three ways to produce three kinds of electric signals, as follows:

1. turn on the switch 22A by pushing the side 25B of the operation knob 25;
2. turn on the switch 22B by pushing the side 25C of the operation knob 25; and
3. Action to turn on both switch 22A and switch 22B by pushing the indented part 25A of the operation knob 25.

When pushing the knob 25, the rotating element 41 of the rotary encoder 27 does not rotate because the detent 45A at the leading end of the click-feeling spring 45 is fitted into the recess of the radial undulated portion 44 at its inner side. Therefore, unintended signals are not generated upon pushing of the knob 25. Moreover, when pushing the operation knob 25, the motion of the rotary encoder 27 due to swinging of the frame 24 is absorbed as the flexible coupling plates 46A, 46B, 46C extending from the plate element 26 are deflected, and hence it is not transmitted to the contact block 28.

Thus, according to the embodiment, by manipulation of only one knob 25, two kinds of electric signals can be generated by rotation of the knob in opposite rotating directions, and three kinds of electric signals can be generated by pushing of the knob at three different pushing positions on the knob.

Therefore, the embodiment realizes a very easy-to-manipulate REPS capable of generating a total of five types of electric signals easily and quickly by using only one knob.

In the rotary encoder 27 discribed above, different electric signals are generated by the rotary operation part depending on the rotating direction of the knob 25, but the same effects can be obtained also in a rotary switch having a contact which moves in the rotating direction when the knob 25 is rotated by a specified angle.

In the foregoing explanation, switches 22A, 22B are formed by putting dome spring type movable contacts 30A and 30B on the fixed contacts 29A, 29B, 29C, and 29D disposed on the top of the base unit 23. Instead of the switches 22A, 22B, two prefabricated switches may be disposed on the base unit 23. Moreover, the switch is not limited to one-circuit type, but in the case of twocircuit or multiple-circuit push switch, more electric signals can be generated by connecting and disconnecting more circuits.

Second Embodiment

Figure 14:
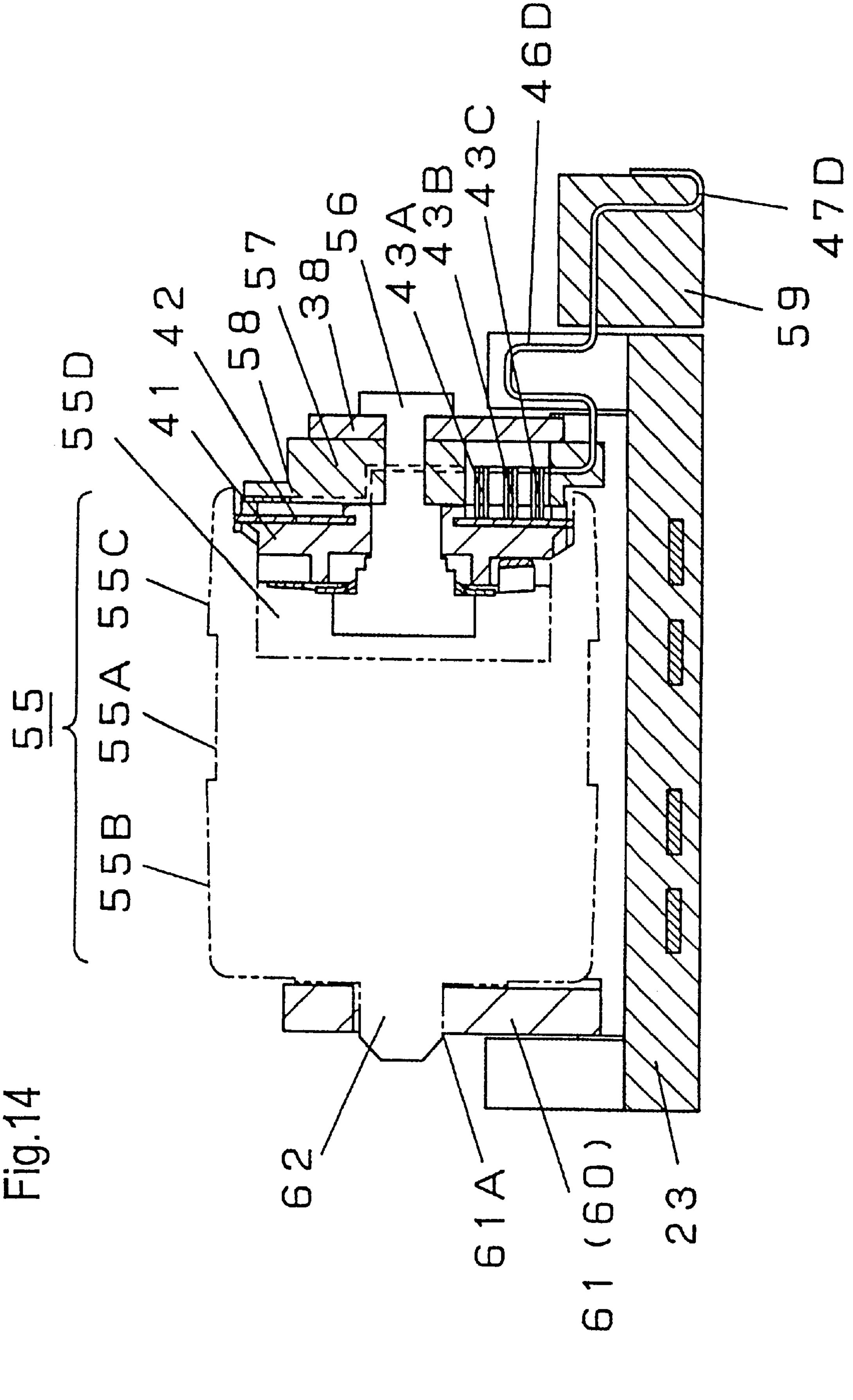
FIG. 14 is a front sectional view of a REPS according to a second embodiment of the present invention.

FIG. 14 is a front sectional view of a REPS 54 which is a rotary-push type electronic component according to a second embodiment of the invention. As compared with the constitution of the first embodiment, the constitution of the second embodiment differs in the following points:

- A grounding plate 58 is added as a measure against static electricity generated when the user of the REPS 54 touches a cylindrical operation knob 55 by hand or finger; and
- the knob 55 can be incorporated after mounting on a wiring board 51 of an electronic appliance in a constitution in which the knob 55 indicated by double dot chain line in FIG. 14 is not supported directly on a shaft 56.

The remaining constitution is same as the REPS 21 in the first embodiment. The same parts as in the first embodiment are identified with the same reference numerals and further explanation thereof is omitted, and only different points are described in detail.

First of all, the grounding plate 58 is disposed by insert forming so as to be exposed on the outer circumferential end portion including the upper end portion of a plate element 57 adjacent to the outer circumference of the upper half of the knob 55. The grounding plate 58 is disposed closer to the outer circumference of the knob 55 than a movable contact (radially-shaped contact plate 42) which is a member of the rotary encoder 27 or fixed contacts (common elastic contact 43A and elastic signal contacts 43B, 43C).

This grounding plate 58 is constituted, like the fixed contacts, so as to be connected to the grounding circuit of the electronic appliance by being connected to a connection terminal 47D at the outer end of a contact block 59 through a flexible coupling plate 46D formed of a thin metal plate 63 integral with the grounding plate 58.

On the other hand, the knob 55 that is indicated generally by double-dot chain lines in FIG. 14 is hollow and open at its end nearest the plate element 57. As in the first embodiment, a rotating element 41 is fitted and coupled so as to close its opening 55D. However, the end portion of the knob 55 nearest the central portion 61 of a U-shaped element 60 (shown in FIG. 16) is closed, and a cylindrical shaft 62 projects into its center. The cylindrical shaft 62 is rotatably held in a bearing hole 61A of the upper opening provided in the central upper part of the central portion 61 of the U-shaped element 60.

The middle portion 55A of the outer circumference of the knob 55 is indented relative to both sides 55B, 55C, as in the first embodiment.

Figure 15A:
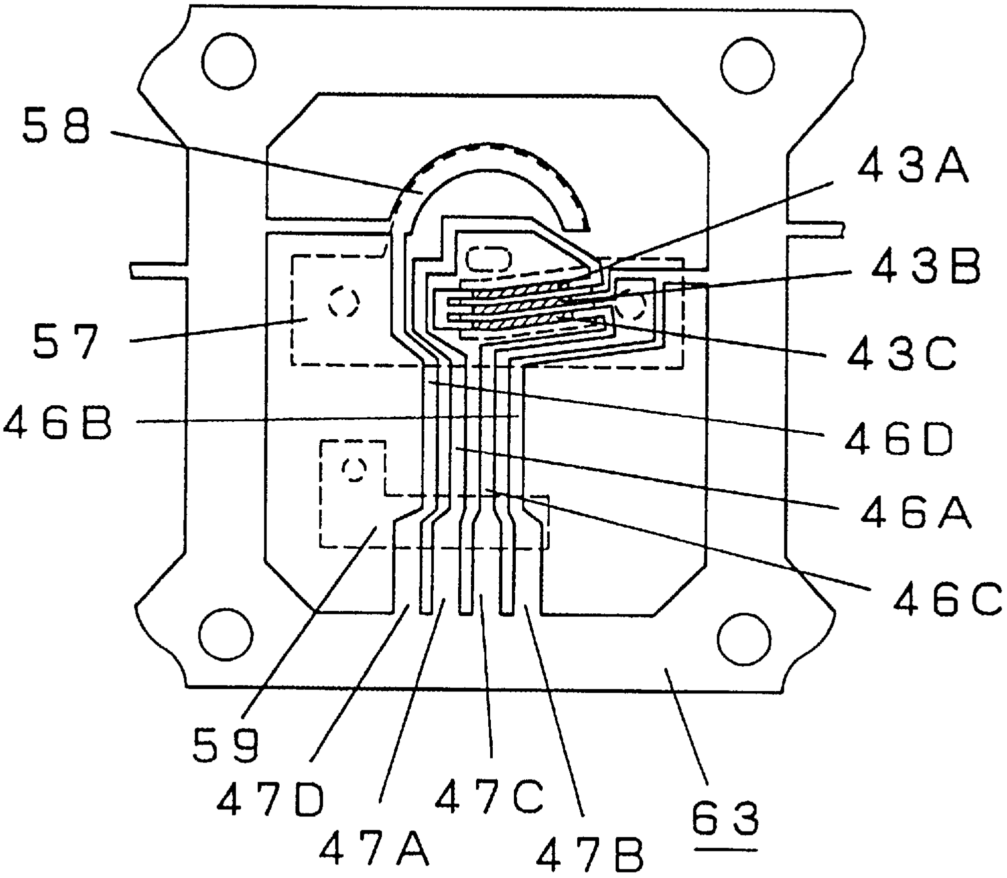
FIG. 15A is an explanatory diagram of a method of forming a plate element and contact block of the second embodiment.
Figure 15B:
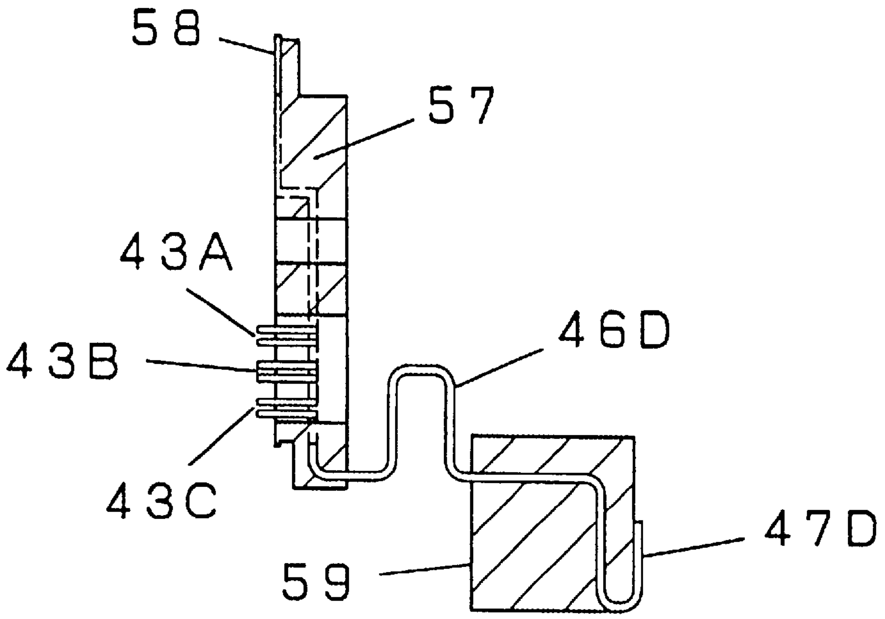
FIG. 15B is a sectional view after cutting and bending of a thin metal plate portion.

Referring now to the explanatory diagram of a method of forming the plate element and contact block of FIG. 15A and FIG. 15B, the method of forming the plate element 57 having the grounding plate 58 is explained below. FIG. 15A shows a plan view of a thin metal plate after a blanking process.

An elastic thin metal plate 63 processed by blanking is composed of the following:

three elastic contacts 43A, 43B, 43C, coupling plates 46A, 46B, 46C, three connection terminals 47A, 47B, 47C, grounding plate 58, coupling plate 46D, and connection terminal 47D.

When forming and processing the portions as the contact block 59 and plate element 57 indicated by dotted lines in FIG. 15A, the thin metal plate 63 is processed by insert forming. After the insert forming process, the thin metal plate parts in FIG. 15B are cut and bent and, as shown in the sectional view, the portions formed as elastic contacts 43A, 43B, 43C are cut and bent, and the middle portions of the coupling plates 46A, 46B, 46C, and 46D are folded and bent into a crankshape. The plate element 57 and contact block 59 are formed in the shape conforming to the complete state of the encoder 64 as in the first embodiment.

A rectangular frame 65 is formed by combining the plate element 57 and U-shaped element 60 and fixing them with a clamp 38. The shaft 56 to be held is fitted through a hole in the plate element 57 of the frame 65 and a hole in the clamp 38 so as not to rotate. The shaft 56 is of such a length as to be disposed within the space of the opening 55D of the knob 55 as shown in FIG. 14. The formed plate element 57 and contact block 59 are assembled in the rotary encoder 64 formed at one end of the frame 65.

Figure 16:
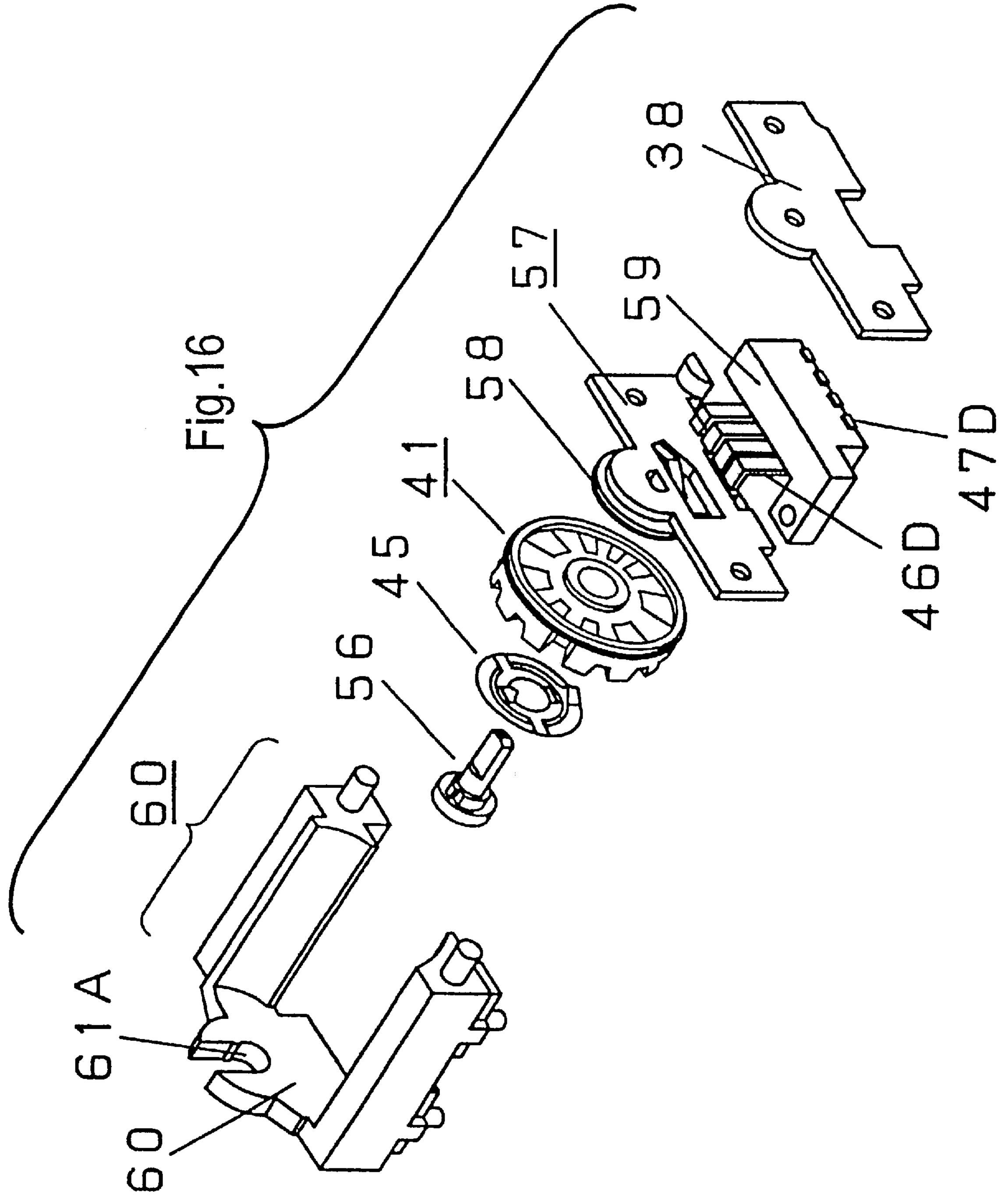
FIG. 16 is a perspective exploded view of a rotary encoder of the second embodiment.

The assembling method is the same as in the first embodiment FIG. 16 is perspective exploded view of the rotary encoder 64. The knob 55 indicated by broken lines is not mounted in this stage.

The REPS 54 of this embodiment is soldered and connected to the wiring board 51 of the electronic appliance before incorporating the knob 55.

Figure 17:
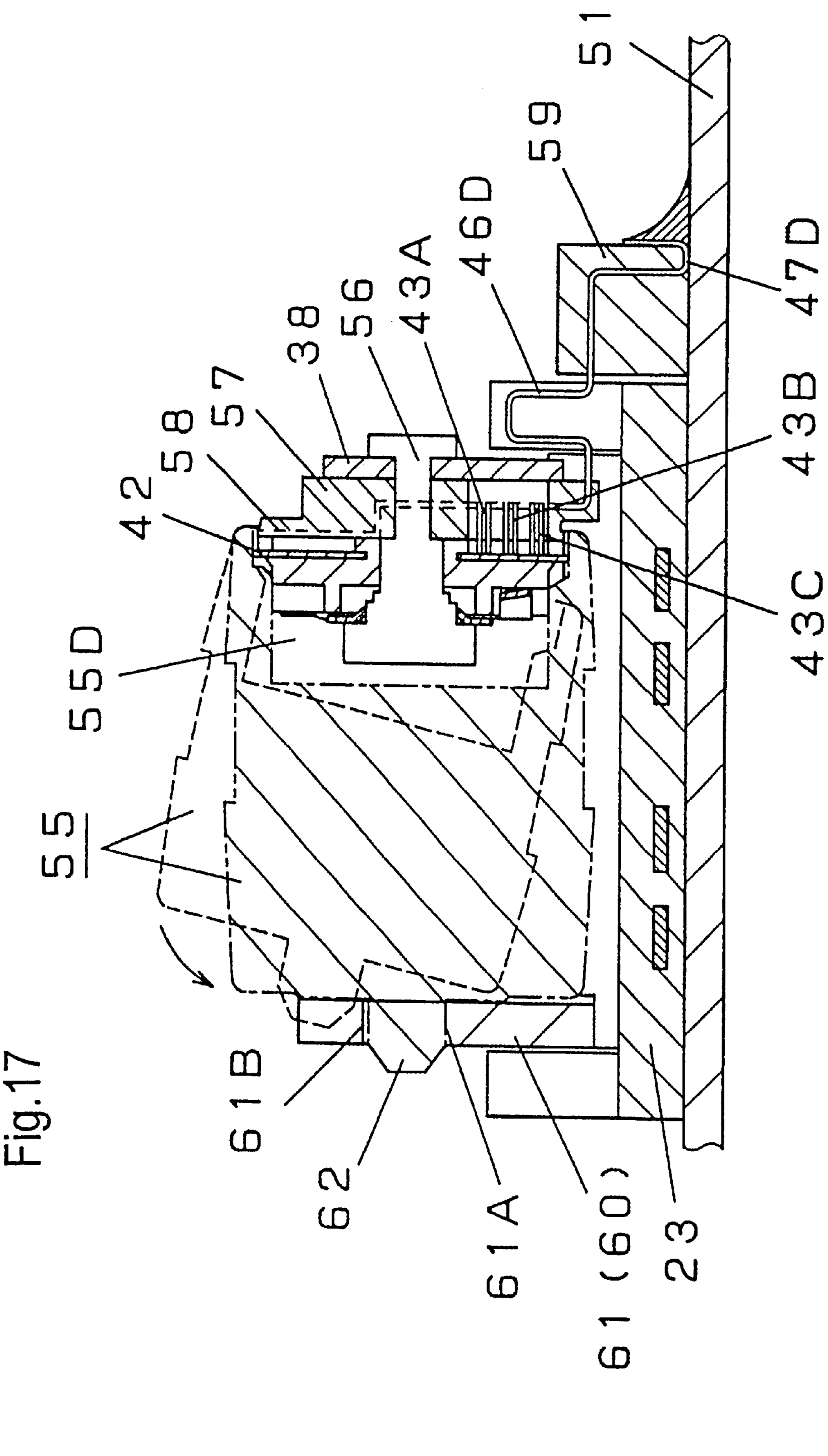
FIG. 17 is a front sectional view showing mounting of the REPS on a wiring board of an electronic appliance.

Next, the knob 55 is installed. As shown in FIG. 17, the knob 55 is first set obliquely, and the rotating element 41 rotatably supported on the shaft 56 is fitted into a hollow opening 55D. The outer circumference of the rotating element 41 is fitted to the inner circumference of the opening 55D. In this state, the cylindrical shaft 62 at the center of the end of the knob 55 is snapped in and coupled to the element 60 by pushing the knob from above into the bearing hole 61A, the inlet to which includes a narrow part 61B. By this manner, the knob 55 is rotatably mounted.

The method of mounting the wiring board 51 of the electronic appliance using the REPS 54 of the second embodiment by inserting the wiring board 51 between the upper case 49 and lower case 50, and the operation of the mounted REPS 54 of the second embodiment are the same as in the first embodiment, and further explanation thereof is omitted.

Thus, in the case of the REPS 54 of the second embodiment used in the electronic appliance, flow of current in the case of generation of static electricity is explained below. When the user touches the upper end portion of the middle portion 55A of the knob 55 during manipulation and static electricity is generated, the static electricity is discharged into the exposed portion of the grounding plate 58 which is the conductive part closest to the surface of the knob 55. The discharge current flows into the grounding circuit of the electronic appliance from the grounding plate 58 through the coupling plate 46D and connection terminal 47D. Therefore, this discharge current does not flow into the circuits of the rotary encoder or electronic appliance. In this embodiment, moreover, the knob 55 can be mounted after soldering and installing the rotary encoder on the wiring board 51 of the electronic appliance. This reduces the possibility of staining or damaging the knob during assembling or handling of the rotary encoder 27. In particular, it can prevent effects of heat on the knob when soldering and connecting the encoder to the wiring board 51 of the electronic appliance, or discoloration or staining of the knob 55 due to scattering of solder or flux.

In the REPS of this embodiment, instead of forming the switch on the top of the base unit 23, a prefabricated switch may be disposed on the base unit 23. Also, more electric signals can be generated when the switch is a multiple-circuit push switch, as in the first embodiment.

Third Embodiment

Figure 18:
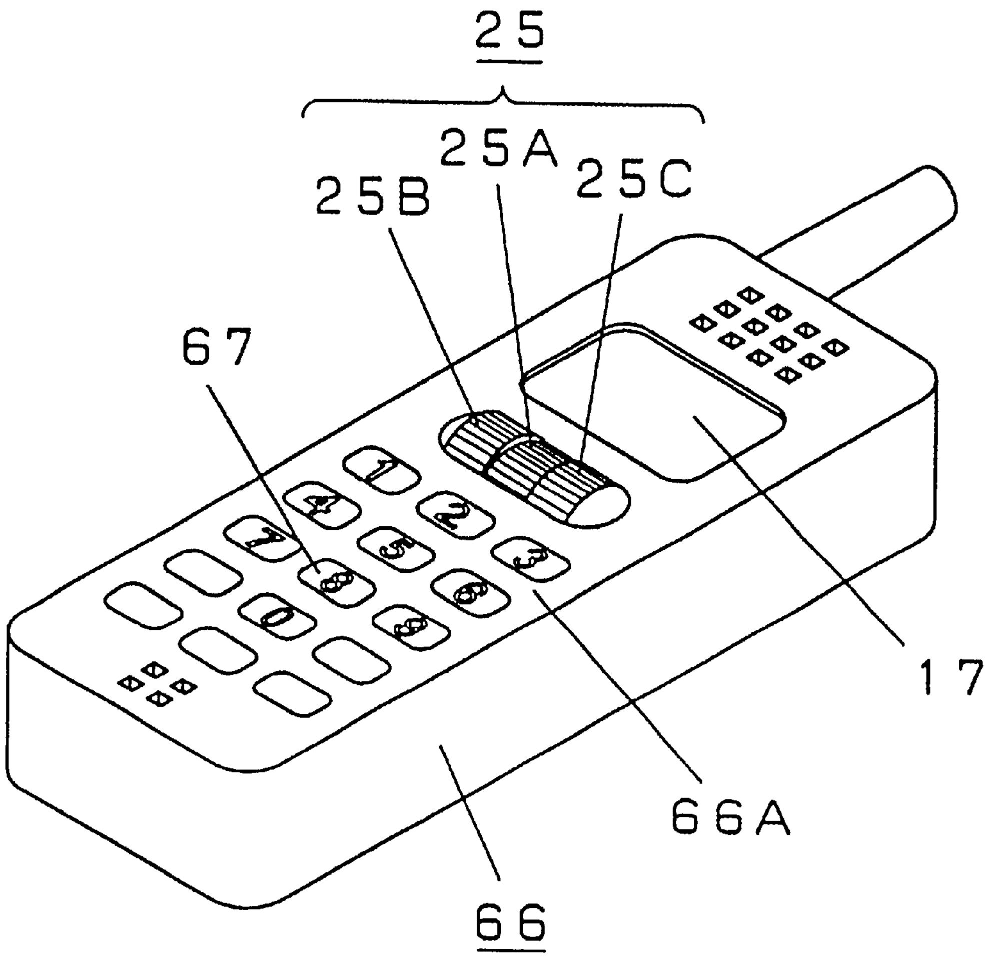
FIG. 18 is a perspective outline view of a mobile telephone as an electronic appliance according to a third embodiment of the present invention.
Figure 19:
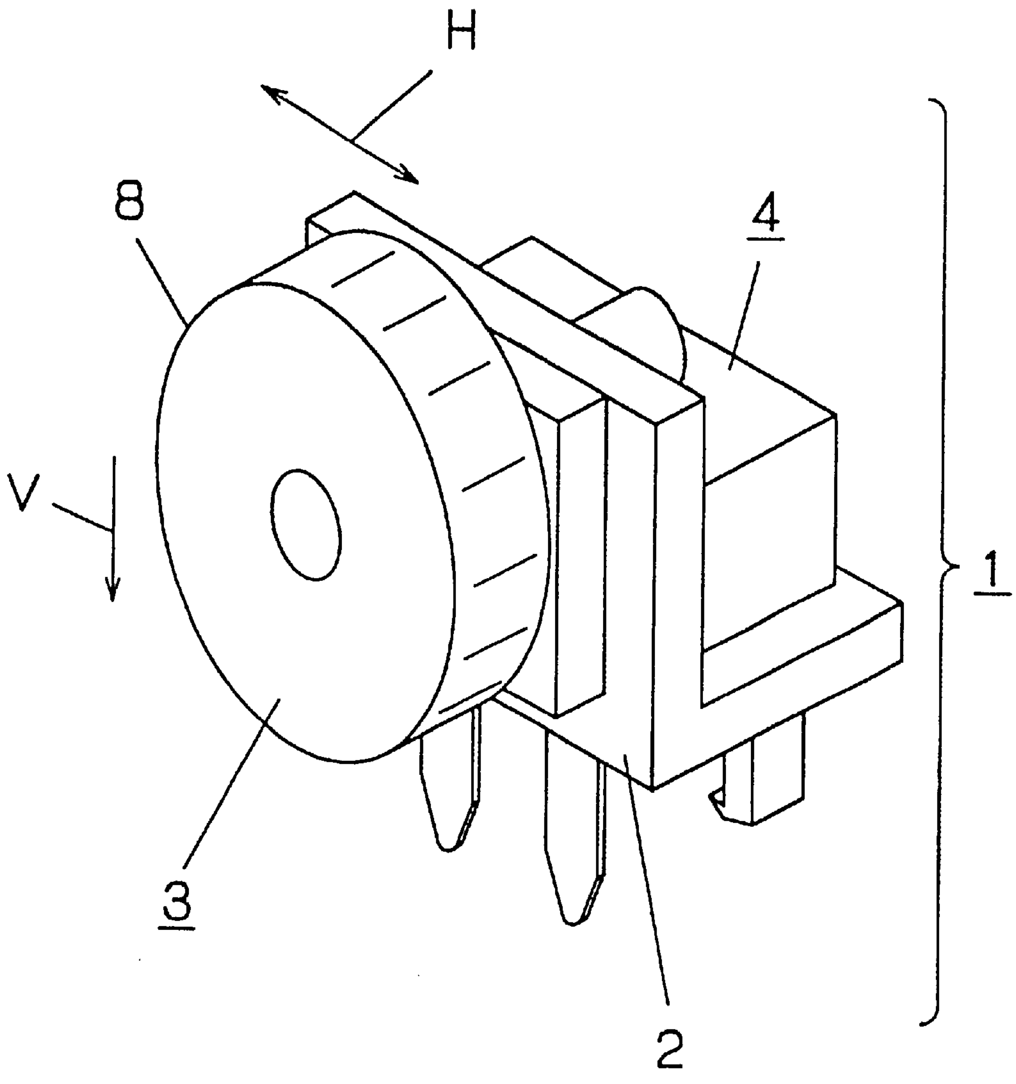
Fig.19 PRIOR ART
FIG. 19 is a perspective outline view of a conventional REPS.
Figure 20:
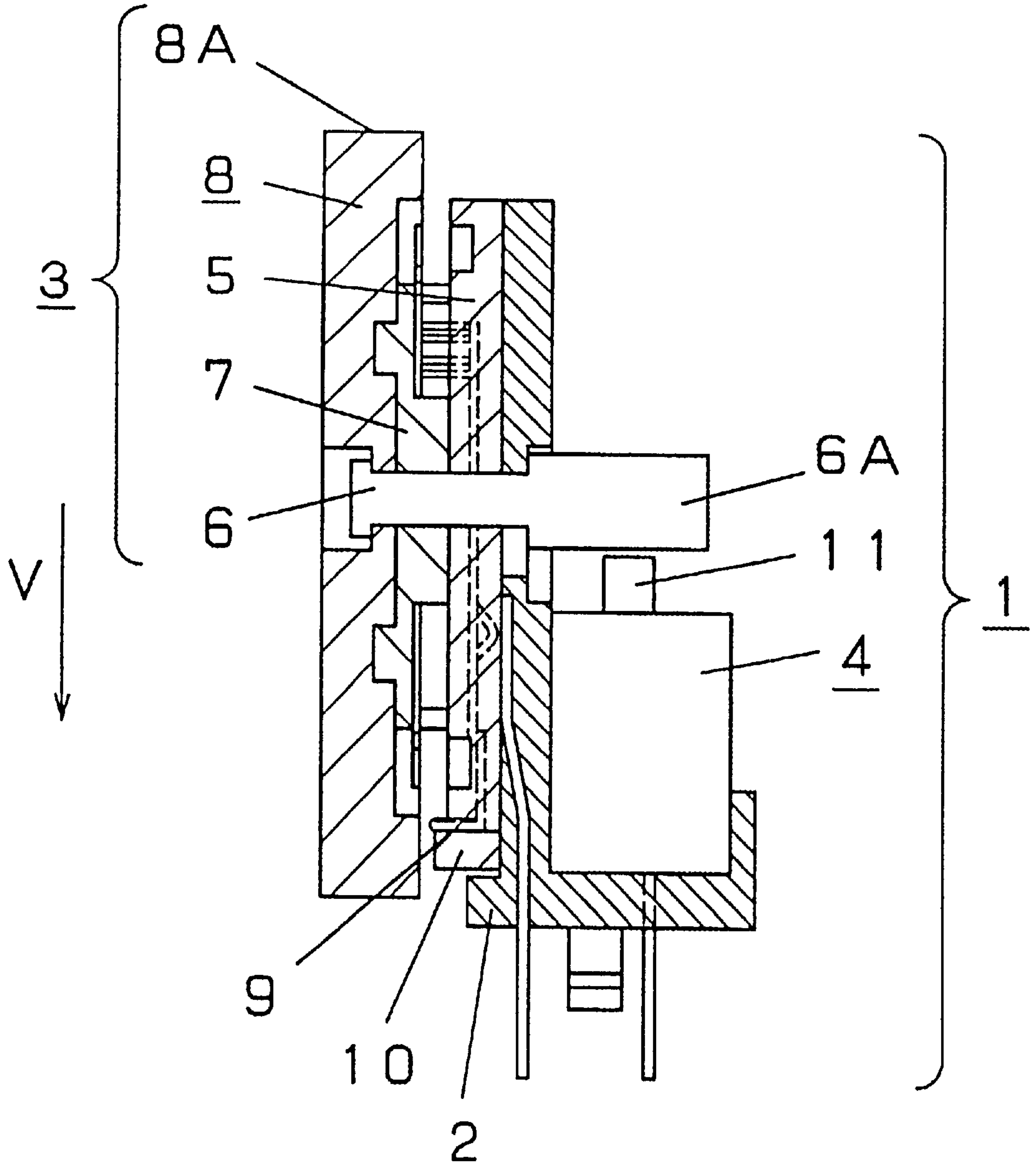
Fig.20 PRIOR ART
FIG. 20 is a side sectional view of the conventional REPS.
Figure 21:
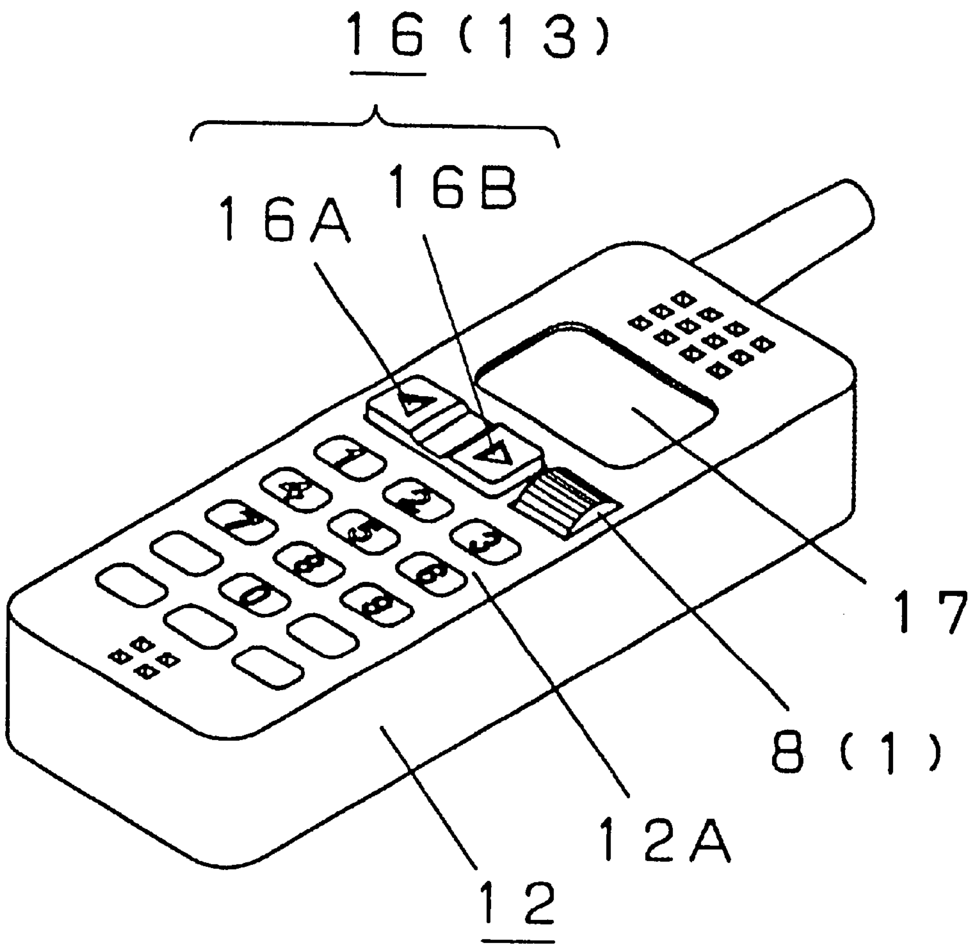
Fig.21 PRIOR ART
FIG. 21 is a perspective outline view of a mobile telephone using the conventional REPS.
Figure 22:
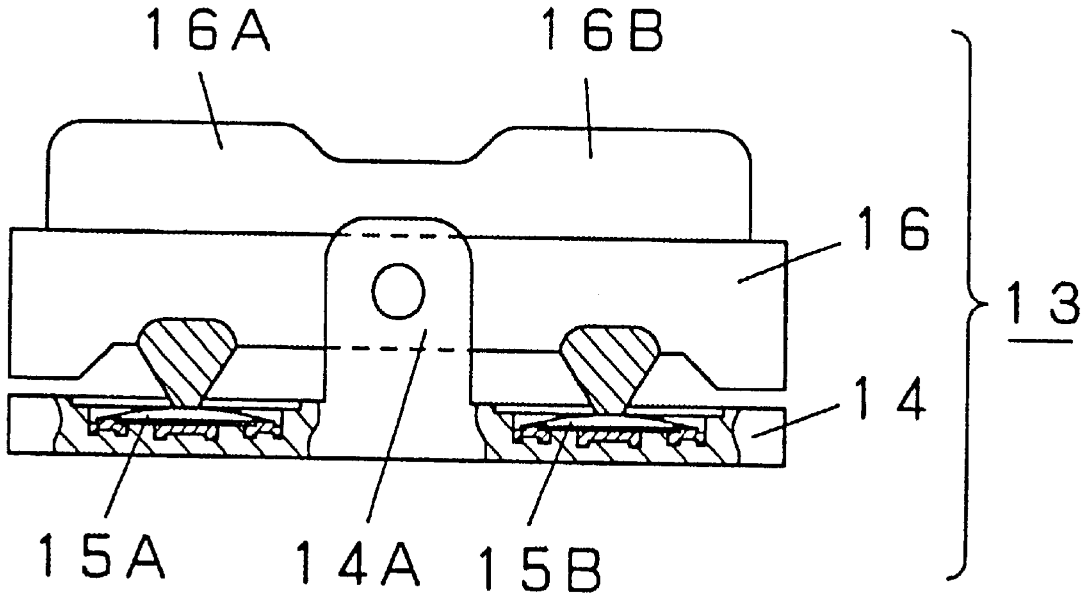
Fig.22 PRIOR ART
FIG 22 is a partially sectional front view of a two-circuit push switch.

FIG. 18 is a perspective outline view of a mobile telephone as an example of an electronic appliance according to a third embodiment of the invention, incorporating a rotary encoder with push switch (REPS) which is a rotary-push type electronic component of the first embodiment of the invention.

As shown in FIG. 18, on an operating surface 66A of the top of a mobile telephone 66, between a liquid crystal display unit 17 and a numeric keypad 67, the upper half of the cylindrical shape of the cylindrical operation knob 25 of the push switch 21 described in the first embodiment is projected.

The method of use of this mobile telephone 66 is explained.

Upon start of use of the mobile telephone 66, when the menu of plural function items is displayed in a specified sequential relation on the liquid crystal display unit 17 of its operating surface 66A, the following actions can be carried out.

1. In the first place, a force in a tangential direction is applied to the upper end portion of the indented middle portion 25A of the outer circumference of the knob 25 projecting from the operating surface 66A.
2. A signal is generated from the rotary encoder 27 by rotating the outer upper surface of the knob 25.
3. Depending on this signal, the function item menu (not shown) in the display screen is displayed. The knob 25 is moved forward or backward to move to the line of a desired item.
4. The switch 22A or 22B is actuated by pushing the upper end portion of the left side 25B or right side 25C of the knob 25.
5. By this switch operation, the function item menu in the display screen (not shown) is moved through in right or left directions to the column of the desired item, and the desired item is selected.
6. For example, at the position for the item "Send", the upper end portion of the middle portion 25A of the knob 25 is pushed, and the two switches 22A, 22B are operated almost simultaneously.
7. Once the Send function is determined, a menu of plural transmission destinations is displayed in the liquid crystal display unit 17 in a specified sequence.
8. A force in a tangential direction is applied again to the upper end portion of the middle portion 25A of the knob 25, such that the knob is rotated.
9. By this operation, the transmission destination menu is moved through in forward or backward directions to the position of a desired destination, which is then selected.
10. At the position of the desired destination, the upper end portion of the middle portion 25A of the knob 25 is pushed again to determine.
11. Then a call signal is sent to the destination.

In the manipulation of the REPS 21, the knob 25 can be pushed in three differentways; that is, the indented middle portion 25A can be pushed, the side 25B can be pushed, and the side 25C can be pushed.

More specifically, when the indented middle portion 25A is pushed, the two switches 22A, 22B are turned on virtually simultaneously. In this operation, the ON timing may be slightly deviated. Accordingly, switching recognition means using time measuring means is provided in order to judge that both switches are ON when the two switches ON within a specific time period. That is, it is intended to distinguish the action of the turning on both switches 22A and 22B by pushing the middle portions 25A from the actions of turning on the switch 22A by pushing the side 25B of the operation knob 25 and turning on the switch 22B by pushing the side 25C of the operation knob 25.

In this constitution, when two push operation parts are manipulated within a specific time, the electric signal may be processed differently from the single electric signal when either push operation part is manipulated.

Thus, the embodiment presents a mobile telephone as an electronic appliance excellent in controllability and with which it is possible to determine a desired selection item easily and quickly from the menu of plural selection items, only by changing the position for manipulating the top of one operation knob 25. In this third embodiment, the REPS of the first embodiment is used in the mobile telephone, but the rotary encoder with push switch in the first embodiment may also be used in other electronic appliances.

Accordingly, the invention brings about a beneficial effect of realizing a rotary encoder with push switch as an electronic component excellent in controllability and with which it is possible to select and determine a desired item easily and quickly, when used in an electronic appliance for selecting and using a specified item from the menu of plural selection items.

What is claimed is:

1. A rotary-push type electronic component comprising:

a base unit;

a frame mounted to said base unit;

a support shaft coupling said frame to said base unit for pivotal movement of said frame relative to said base unit and for vertical movement of said frame relative to said base unit through a given range;

a generally cylindrical operation knob having a rotation axis, said generally cylindrical operation knob being rotatably mounted to said frame for rotation about said rotation axis;

a rotary operation device, including a fixed part fixed to said frame and a movable part coupled to said generally cylindrical operation knob for rotation therewith relative to said fixed part, for emitting an electrical signal upon rotation of said generally cylindrical operation knob;

a pair of self-restoring push operation parts spaced apart on said base unit below said frame so as to be operated by pivoting of said frame about said support shaft relative to said base unit;

wherein said frame includes front and rear end portions and first and second side portions;

wherein said support shaft is disposed at said rear end portion of said frame; and wherein said self-restoring push operation parts are disposed beneath said front end portion of said frame.

2. A rotary-push type electronic component according to claim 1, wherein said fixed part of said rotary operation device comprises a fixed contact; and said movable part of said rotary operation device comprises a movable contact arranged for contact with said fixed contact of said rotary operation device.

3. A rotary-push type electronic component according to claim 2, wherein said frame comprises a generally rectangular frame.

4. A rotary-push type electronic component according to claim 1, wherein said generally cylindrical operation knob is mounted to said frame, said frame is pivotally and vertically movably mounted to said base unit, and said two push operation parts are disposed beneath said frame, in such a manner that:

one of said push operation parts can be operated individually by pushing an outer upper surface of said generally cylindrical operation knob downward at a first axial end portion thereof;

the other of said push operation parts can be operated individually by pushing an outer upper surface of said generally cylindrical operation knob downward at a second axial end portion thereof; and both of said push operation parts can be operated simultaneously by pushing an outer upper surface of said generally cylindrical operation knob downward at an axially central portion thereof.

5. A rotary-push type electronic component according to claim 4, wherein said axially central portion of said outer upper surface of said generally cylindrical operation knob is indented relative to said first and second axial end portions thereof.

6. A rotary-push type electronic component according to claim 4, wherein said axially central portion of said outer upper surface of said generally cylindrical operation knob comprises a touch discernment part enabling a user to discern by touch said axially central portion from said first and second axial end portions of said outer upper surface of said generally cylindrical operation knob;

said support shaft includes two opposite ends supporting said frame on said base unit at two spaced-apart support locations; and a distance between said spaced-apart support locations is at least as long as an axial length of said axially central portion of said outer upper surface of said generally cylindrical operation knob.

7. A rotary-push type electronic component according to claim 4, wherein said frame comprises a U-shaped element at said front and rear end portions and said first side portion thereof, and a plate element closing an open end of said U-shaped element at said second side portion of said frame; and said fixed part of said rotary operation device is provided at said plate element.

8. A rotary-push type electronic component according to claim 4, wherein one end of said generally cylindrical operation knob has said movable part of said rotary operation device pressed thereinto, and the other end of said generally cylindrical operation knob has a snap-in coupling part for snap-in coupling of said generally cylindrical operation knob to said frame from above, such that said generally cylindrical operation knob is detachable from said frame.

9. A rotary-push type electronic component according to claim 4, wherein a spring is provided for urging said rear end portion of said frame downwardly toward said frame with an urging force greater than an operation force of said push operation parts, so that both ends of said frame are normally positioned at a lower end of said given range of vertical movement.

10. A rotary-push type electronic component according to claim 4, further comprising click-feeling element operably coupled to said generally cylindrical operation knob for generating a click feel during rotation of said generally cylindrical operation knob.

11. A rotary-push type electronic component according to claim 4, wherein said rotary operation device comprises a rotary encoder for generating different signals depending on a rotating direction of said generally cylindrical operation knob; and each of said self-restoring push operation parts comprises a push switch.

12. A rotary-push type electronic component according to claim 11, wherein each of said push switches comprises a fixed contact and a dome spring type movable contact formed of an elastic thin metal plate and disposed over said fixed contact; and a flexible film is covered over an upper surface of said dome spring type movable contact, and an adhesive is provided on a lower surface of said flexible film.

13. A rotary-push type electronic component according to claim 4, wherein said fixed part of said rotary operation device comprises a fixed contact, and said movable part of said rotary operation device comprises a movable contact arranged for contact with said fixed contact of said rotary operation device;

said rotary operation device comprises a rotary switch operable such that, upon rotation of said generally cylindrical operation knob by a specified angle, said movable part moves in the direction of rotation of said generally cylindrical operation knob; and each of said self-restoring push operation parts comprises a push switch.

14. A rotary-push type electronic component according to claim 13, wherein each of said push switches comprises a fixed contact and a dome spring type movable contact formed of an elastic thin metal plate and disposed over said fixed contact; and a flexible film is covered over an upper surface of said dome spring type movable contact, and an adhesive is provided on a lower surface of said flexible film.

15. A rotary-push type electronic component according to claim 4, further comprising a contact block for connection to an external circuit;

a thin metal coupling plate formed integrally with said fixed part of said rotary operation device and electrically coupling said fixed part of said rotary operation device with said contact block.

16. A rotary-push type electronic component according to claim 15, further comprising a grounding plate disposed between said outer upper surface of said generally cylindrical operation knob and said movable part of said rotary operation device; and a contact coupled to said contact block for connecting said grounding plate to a grounding circuit of an electronic appliance.

17. An electronic appliance comprising a rotary-push type electronic component according to claim 16, and further comprising a case including an upper case and a lower case;

a wiring board disposed in said lower case;

wherein said contact block is fixed to said base unit and is physically and electrically connected to said wiring board; and wherein connection terminals of said push operation parts are electrically connected to said wiring board.

18. An electronic appliance comprising a rotary-push type electronic component according to claim 15, and further comprising a case including an upper case and a lower case;

a wiring board disposed in said lower case;

wherein said contact block is fixed to said base unit and is physically and electrically connected to said wiring board; and wherein connection terminals of said push operation parts are electrically connected to said wiring board.

19. An electronic appliance comprising a rotary-push type electronic component according to claim 4, and further comprising a case including an upper case and a lower case; and a positioning engaging part provided between said base unit and said upper case for positioning said rotary-push type electronic component within said case.

20. An electronic appliance comprising a rotary-push type electronic component according to claim 4, and further comprising a case including an upper case and a lower case; and at least one cover portion formed integrally with said upper case and covering axially opposing ends of said generally cylindrical operation knob.

21. An electronic appliance comprising a rotary-push type electronic component according to claim 4, and further comprising a switching recognition device comprising a time measurement part for processing a signal generated when both of said push operation parts are operated within a specified time period differently than signals generated when one of said push operation parts is operated individually without the other of said push operation parts being operated within said specified time period of the operation of said one of said push operation parts.

22. An electronic appliance according to claim 21, further comprising a main body display unit for displaying a sequentially arranged menu of selection items;

wherein said rotary operation device is operable to, upon rotation of said generally cylindrical operation knob in a first rotary direction by pushing said outer upper surface in a first tangential direction, generate a first signal to cause scrolling through said selection items in a first direction, and, upon rotation of said generally cylindrical operation knob in a second rotary direction by pushing said outer upper surface in a second tangential direction, generate a second signal to cause scrolling through said selection items in a second direction opposite said first direction;

wherein said push operation parts are operable to, upon downward pushing of said outer upper surface of said generally cylindrical operation knob at said first axial end portion thereof, generate a third signal to cause scrolling through said selection items in a third direction orthogonal to said first and second directions, and, upon downward pushing of said outer upper surface of said generally cylindrical operation knob at said second axial end portion thereof, generate a fourth signal to cause scrolling through said selection items in a fourth direction opposite said third direction, and, upon downward pushing of said outer upper surface of said generally cylindrical operation knob at said axially central portion thereof, generate a fifth signal to determine selection of one of said selection items.

* * * * *